US005645702A

United States Patent [19]
Witt et al.

[11] Patent Number: 5,645,702
[45] Date of Patent: Jul. 8, 1997

[54] LOW VOLTAGE MINIATURIZED COLUMN ANALYTICAL APPARATUS AND METHOD

[75] Inventors: Klaus E. Witt, Keltern; Patrick Kaltenbach, Bischweier; Fritz Bek, Waldbronn, all of Germany; Sally A. Swedberg, Los Altos; Laurie S. Mittelstadt, Belmont, both of Calif.

[73] Assignee: Hewlett-Packard Company, Palo Alto, Calif.

[21] Appl. No.: 483,217

[22] Filed: Jun. 7, 1995

[51] Int. Cl.$^6$ .......................... G01N 27/26; G01N 27/447
[52] U.S. Cl. .......................... 204/501; 204/500; 204/600; 204/601
[58] Field of Search ........................ 204/299 R, 180.1

[56] References Cited

U.S. PATENT DOCUMENTS

| | | | |
|---|---|---|---|
| 3,846,274 | 11/1974 | Gifford | 204/645 |
| 4,390,403 | 6/1983 | Batchelder | 204/547 |
| 4,471,647 | 9/1984 | Jerman et al. | 374/135 X |
| 4,474,889 | 10/1984 | Terry et al. | 436/161 |
| 4,740,283 | 4/1988 | Laas | 204/458 |
| 4,834,862 | 5/1989 | Breiner et al. | 204/548 |
| 4,891,120 | 1/1990 | Sethi et al. | 204/600 |
| 4,908,112 | 3/1990 | Pace | 204/601 X |
| 4,911,817 | 3/1990 | Kindlmann | 204/607 |
| 4,935,040 | 6/1990 | Goedert | 55/270 X |
| 5,126,022 | 6/1992 | Soane et al. | 204/458 |
| 5,132,012 | 7/1992 | Miura et al. | 210/198.2 |
| 5,194,133 | 3/1993 | Clark et al. | 204/608 |
| 5,328,578 | 7/1994 | Gordon | 204/452 |
| 5,454,472 | 10/1995 | Benecke et al. | 209/127.1 |

FOREIGN PATENT DOCUMENTS

| | | |
|---|---|---|
| WO84/02001 | 5/1984 | European Pat. Off. . |
| 0 356 187 | 2/1990 | European Pat. Off. . |
| 0 361 046 | 4/1990 | European Pat. Off. . |
| 376611 | 7/1990 | European Pat. Off. . |
| WO93/25899 | 12/1993 | European Pat. Off. . |
| 268877 | 6/1989 | Germany . |
| 9207657 | 5/1992 | Germany .................. 204/299 R |
| 0 376 611 | 12/1989 | United Kingdom . |
| 0 558 233 A1 | 2/1993 | United Kingdom . |
| 2264783 | 9/1993 | United Kingdom .................. 204/299 R |

OTHER PUBLICATIONS

James R. Melcher, "Traveling-Wave Induced Electro Convection" The Physics of Fluids, vol. 9, No. 8 (Aug. 1966) 1548–1555.

Rolf Hagedorn et al "Traveling-Wave dielectrophoresis of microparticles" Electrophoresis 1992, vol. 13 (1992) 49–54.

Senichi Masuda et al "Movement of Blood Cells in Liquid by Nonuniform Traveling Field" IEEE Transactions on Industry Applications, vol. 24, No. 2 (Mar./Apr. 1988) 217–222.

Danel et al. "Quartz: a material for microdevices" (1991) *J. Micromech. Microeng.*, 187–198.

Fan et al. "Micromachining of Capillary Electrophoresis Injectors and Separators on Glass Chips and Evaluation of Flow at Capillary Intersections" *Anal Chem.* (1994) 66:177–184.

Frazier et al. "Development of micromachined devices using polyimide-based process" Sensors and Actuators (1994) A45:47–55.

Jacobson et al. "Precolumn Reactions with Electrophoretic Analysis Integrated on a Microchip" *Anal. Chem.* (1994) 66:4127–4132.

Harrison et al. "Towards miniaturized electrophoresis and chemical analysis systems on silicon; an alternative to chemical sensors" Sensors and Actuators B (1993) 10:107–116.

Manz et al. "Design of an Open-tubular Col. Liquid Chromatograph Using Silicon Chip Technology" *Sensors and Actuators, B1* (1990) 249–255.

Manz et al. "Micromachining of monocrystalline silicon and glass for chemical analysis sytems" *Trends in Anal. Chem.* 10(5) 1991, pp. 144–149.

Manz et al. "Planar Chips Technology for Miniaturization of Separation Systems: A Developing Perspective in Chemical Monitoring" *Advances in Chromatography* (1993) vol. 33, pp. 1–66.

Petersen, Kurt "Silicon as a Mechanical Material" *Proceedings of the IEEE*, vol. 70, No. 5, May 1982, pp. 420–457.

*Primary Examiner*—Kathryn L. Gorgos
*Assistant Examiner*—John S. Starsiak, Jr.

[57] ABSTRACT

A miniaturized column analytical apparatus having a miniaturized column device containing a body with an elongate separation compartment is provided. Two or more sets of spaced apart antennas are positioned along the elongate separation compartment. The elongate separation compartment has first and second opposing sides along its elongate dimension. Each set of antenna contains a plurality of antennas. One antenna from each set is associated with at least one antenna from each of the other sets to form repeating sequences of antennas along the separation compartment on the opposing sides of the separation compartment. Each set of the antennas is associated with a different oscillating electrical potential to provide a plurality of oscillating electric fields along the elongate separation compartment to draw a target substance along the elongate separation compartment toward an exit end of the separation compartment. The detector can detect a target substance passing out of the elongate separation compartment.

30 Claims, 14 Drawing Sheets

LOW VOLTAGE MINIATURIZED COLUMN ANALYTICAL APPARATUS AND METHOD

FIELD OF THE INVENTION

The present invention relates generally to miniaturized column technology for liquid phase analysis. More particularly, this invention relates to method and means of moving charged substances through a miniaturized column in analysis of electrically charged solutes in the liquid phase.

BACKGROUND

In sample analysis instrumentation, especially in separation systems such as liquid chromatography and capillary electrophoresis systems, smaller dimensions will generally result in improved performance characteristics and at the same time result in reduced production and analysis costs. Miniaturized separation systems provide more effective system design, result in lower overhead due to decreased instrumentation sizing and additionally enable increased speed of analysis, decreased sample and solvent consumption and the possibility of increased detection efficiency.

The conventional approach in miniaturization technology for liquid phase analysis is to use drawn fused-silica capillary. An evolving approach is to use silicon micromachining. To enable even greater reduction in separation system sizes, there has been a trend towards providing planarized systems having capillary separation microstructures. Production of miniaturized separation systems involving fabrication of microstructures in silicon by micromachining or microlithographic techniques has been described. Such techniques can include processes such as ithography, molding, and etching. See, e.g. Fan et al., *Anal. Chem.* 66(1):177–184 (1994); Manz et al., *Adv. in Chrom.* 33:1–66 (1993); Harrison et al., *Sens. Actuators, B* B10(2):107–116 (1993); Manz et at., *Trends Anal. Chem.* 10(5):144–149 (1991); and Manz et at., *Sensors and Actuators B (Chemical)* B1(1–6):249–255 (1990). The use of micromachining techniques to fabricate miniaturized separation devices on silicon or borosilicate glass chips can be found in U.S. Pat. Nos. 5,194,133 to Clark et al.; 5,132,012 to Miura et al.; in 4,908,112 to Pace; and in 4,891,120 to Sethi et al.

Because electrophoretic techniques are based on the effect of electric fields on charged particles, another approach to improve performance of electrophoretic systems is by obtaining better interaction between an electric field and the molecules of interest. PCT Publication No. WO 93/25899 describes a technique involving a time-varying field strength that may progressively increase or decrease as a function of time. One electrode each is located at each end of a electrophoretic capillary to provide the electric field. However, in such a system, high voltage is needed to drive the target substances (negatively charged DNA molecules) through the capillary.

U.S. Pat. No. 5,328,578 to Gordon discloses a capillary electrophoresis system utilizing a square ring capillary. The capillary has a hair-pin bend at each corner of the square. An opening at each bend permits fluid and electrical coupling with electrolyte outside the capillary. By switching from applying a voltage differential between selected corners, a sample is caused to repeatedly traverse the ring until satisfactory resolution has been achieved. However, to provide a high electric field in this system, the voltage differential between the electrodes still have to be large. Furthermore, it is necessary to estimate when the sample is between the corners so that the time for switching can be determined.

U.S. Pat. No. 5,126,022 to Soane et al. discloses a technique for moving charged molecules through a medium by the application of a plurality of electrical fields. A large number of electrodes are arranged along a trench or cylinder filled with medium to generate a traveling electrical wave which moves in a single direction along the trench or cylinder. To effectively use such a system, sophisticated computer equipment may be needed to move the electrical waves along the trench or cylinder.

The devices of U.S. Pat. Nos. 5,328,578 and 5,126,022 all involve relatively large conduits containing medium and are unrelated to miniaturized systems. To solve the problems in prior art electrophoresis techniques, the present invention provides electrophoretic systems capable of using easily controlled, low voltage power supply to achieve high electric field, especially such electrophoretic systems applicable in a miniaturize column separation system.

SUMMARY

The present invention provides a miniaturized column device. The miniaturized column device contains a body with an elongate separation compartment and two or more sets of spaced apart antennas along the elongate separation compartment. The elongate separation compartment has first and second opposing sides along its elongate dimension. Each set of antenna contains a plurality of antennas. One antenna from each set is associated with at least one antenna from each of the other sets to form repeating sequences of antennas along the separation compartment on the opposing sides of the separation compartment. Each set of the antennas is associated with a different oscillating electrical potential to provide a plurality of oscillating electric fields along the elongate separation compartment to draw a target substance along the elongate separation compartment toward an exit end of the separation compartment. The detector can detect the target substance.

The present invention also provides a miniaturized column analytical apparatus that has a miniaturized column device of the present invention and a detector.

A method of analyzing a target substance is also provided by the present invention. The steps of the method include placing the target substance in the miniaturized elongate compartment; providing a different oscillating electrical potential on each of two or more sets of antennas along the elongate compartment to result in a plurality of oscillating electric fields to draw the target substance along the elongate compartment; and detecting the target substance at an exit end of the elongate compartment.

The present invention further provides a method of making a miniaturized column device. The method includes the following steps. The first step is to micromachine (e.g., by etching or laser ablation) a substrate on its substantially planar surface to result in a microchannel in the first planar surface. Then a cover member is arranged over the micromachined planar surface. The cover member in combination with the microchannel defines an elongate separation compartment. The separation compartment has first and second opposing sides along its elongate dimension. Positioned along the opposing sides of the separation compartment are two or more sets of spaced apart antennas, each of which contains a plurality of antennas. One antenna from each set is associated with at least one antenna from each of the other sets to form repeating sequences of antennas along the separation compartment at the opposing sides. Then a power supply is connected to the antennas such that each set of the antennas is associated with a different oscillating electrical potential to result in a plurality of oscillating electric fields along the elongate separation compartment. The oscillating electric fields are capable of drawing a target substance along the elongate separation compartment so that the target substance can be detected at an exit end of the elongated separation compartment.

The miniaturized column device and the miniaturized column analytical apparatus of the present invention can be advantageously used to analyze a wide variety of target substances in a liquid medium. Such substances include, but are not limited to, proteins, nucleic acids, polynucleotides, DNA molecules and fragments, and other substantially organic or inorganic molecules that can be present in a charged form for liquid phase analysis. The utilization of oscillating electrical potential affords a good resolution of target substances in a sample. By tuning the frequency of oscillation to the specific frequencies that specific target substance will selectively respond, a wide variety of target substances can be separated in a sample.

Because oscillating electrical potentials are used, relatively simple control equipment will suffice to control the varying electrical potentials. Moreover, due to the large number of evenly spaced antennas, superior analytical results can be obtained because high electric fields can be uniformly distributed over a electrophoretic channel. This is accomplished with the application of low (compared to conventional electrophoresis) voltages (e.g. 10 Volts) to the miniaturized column device. As a result, relatively simple, easily manufactured, and inexpensive equipment can be used to perform high resolution electrophoresis.

In the present invention, the antennas are preferably positioned close to the separation compartment without actually protruding through the surface of the microchannel, thus avoiding the risk of contacting any medium in the separation compartment. Contact of antennas with the medium is undesirable because this will lead to electrolysis and formation of gas bubbles, as well as corrosion of the antennas. In a miniaturized column device, because of the small size of the separation compartment, bubbles will not only distort the path of the fluid, but may actually block the flow. Furthermore, electrode corrosion involves chemical changes in the separation compartment, which may lead to in irreproducibility of analysis results. Thus, with the present invention, high electric fields can be generated without the problems of electrolysis and corrosion. By using oscillating electrical potentials, the antennas can quickly charge and discharge even without the benefit of electrolytes carries charges to or away from the antennas as in prior art medium-contacting electrodes.

Furthermore, in the preferred embodiment of the present invention, by laser ablation, separation compartment and antennas can be formed with very well defined geometry. Use of laser ablation techniques to form miniaturized devices affords several advantages over prior art etching and micromachining techniques. It avoids problems of undercutting masking during etching which may give rise to asymmetrical structures having curved side walls and flat bottoms. Laser ablation further enables the creation of microstructures with greatly reduced component size. In this regard, microstructures formed according to the invention are capable of having aspect ratios several orders of magnitude higher than possible using prior etching techniques, thereby providing enhanced separation capabilities in such devices. By using laser ablation, a larger number of antennas can be formed per centimeter of the separation compartment. Further, it permits the antennas to be positioned very close to the separation compartment without the risk of contacting the medium contained therein.

By positioning a large number of antennas on opposing sides of a separation compartment defined by a microchannel to generate oscillating electric fields, a highly efficient way of separating analytes in a sample results. Since there is no substantial tendency to bias the analytes to only one side of the microchannel, distortion of the flow pattern is reduced. Thus, in this invention, miniaturized column devices with columns of 10 to 20 times shorter than conventional electrophoretic columns (but with comparable resolution) can be made. This can result in, for example, a straight miniaturized column of 1 to 5 cm long. Such small columns will be very useful in applications in a nonlaboratory environment (e.g., in the field, such as a hazardous waste site).

BRIEF DESCRIPTION OF THE DRAWING

The following figures show the embodiments of the present invention to better illustrate the present invention. In these figures, wherein like numerals represent like features in the several views and the structures are not drawn in scale.

DETAILED DESCRIPTION OF THE INVENTION

According to the present invention, oscillating electric fields are provided along an elongate separating compartment to draw a target substance along. The oscillating electric fields result from oscillating electrical potentials applied to antennas positioned along opposing sides of the separating compartments. This technique is particularly well suited for analyzing target substances in a microchannel in a planar miniaturized column device.

Oscillating Electrical Potential to Provide Oscillating Electric Field

Figure 1:
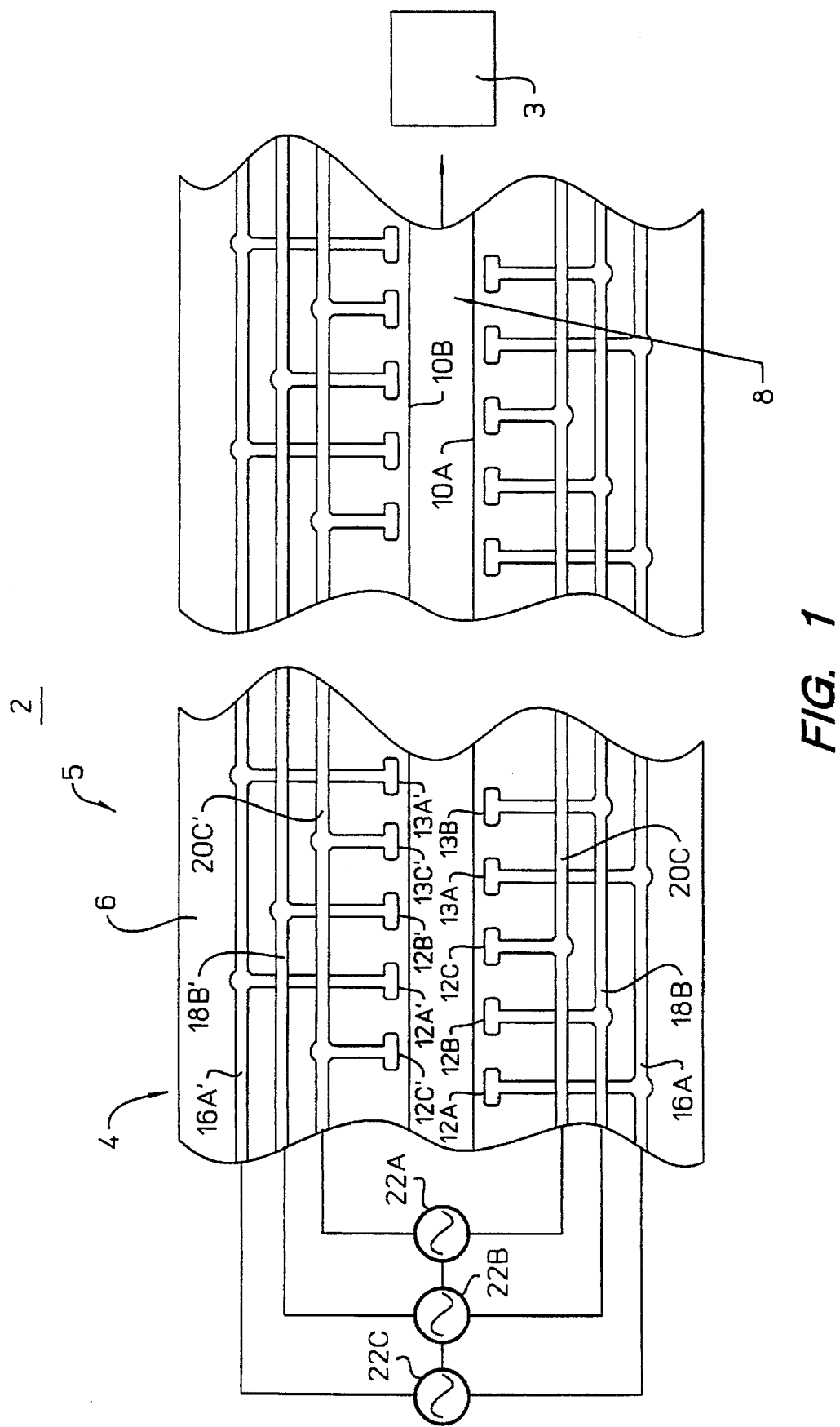
FIG. 1 is a schematic representation in portion of an embodiment of a miniaturized column analytical apparatus having a miniaturized column device constructed in accordance with the present invention.

The following embodiments are provided to illustrate how a miniaturized column device can be used for analyzing target substances according to the present invention. FIG. 1 is a schematic representation of an embodiment of a miniaturized column analytical apparatus according to the present invention. The miniaturized column analytical apparatus 2 includes a detector 3 for detecting a target substance and a miniaturized column device 5. The miniaturized column device 5 (hereinafter referred to as "MCD") has a body 4 including a substrate 6 having an elongate separation compartment 8 therein. The elongate separation compartment 8 has opposing sides 10A, 10B facing each other. At the opposing sides 10A, 10B of the elongate separation compartments along the elongate dimension are positioned a plurality of antennas (or field pads) 12A, 12A', 12B, 12B', 12C, 12C', etc. These antennas differ from electrodes in conventional electrophoretic devices in that they do not directly contact any medium in the separation compartment.

In the body 4 are also a plurality of electrical connectors (or conduits) connecting to the antennas for providing a plurality of electrical potentials thereto. In this embodiments, three strips of electrical connectors 16A, 16B, 16C and 16A', 16B', 16C' are provided at each of the opposing sides of the elongate separation compartment 8. These strips are electrically isolated from one another. Regarding the antennas, every third one on the same side of the elongate separation compartment 8 is connected to the same connector to have the same electrical potential. Thus, in FIG. 1, on side 10A of the separation compartment 8, antennas 12A, 13A, etc. are connected to connector 16A, antennas 12B, 13B, etc. are connected to connector 18B, and antennas 12C, etc. are connected to connector 20C. On the opposing side 10B of the elongate separation compartment 8, antennas 12A', 13A', etc. are connected to connector 16A'. Antennas 12B', etc. are connected to connector 18B'. Antennas 12C', 13C', etc. are connected to connector 20C'.

Connectors 20C and 20C' are connected to the two opposing poles of an oscillating signal generator 22A so that an oscillating electrical potential results across 16A and 16A'. In other words, the signal at connector 16A varies relative to connector 16A' with a repeating wave form around a reference (e.g., 0 (zero), or any offset voltage) electrical potential point. Similarly, connectors 18B and 18B' are connected to the two opposing poles of an electrical signal generator 22B and connector 20C and 20C' are connected to the two opposing poles of the electrical signal generator 22C. Signal generators 22A, 22B, 22C are electrically connected so that they generate oscillating potentials about a common (or reference) electrical potential point (e.g., ground). In this way, the antennas can be grouped into three different sets, each of which being associated with a different electrical potential and having a set phase shift to each other.

Preferably, as shown in FIG. 1, on each opposing side of the elongate separation compartment 8, the antennas are arranged in a single file along the elongate dimension of the separation compartment. Also preferably, the antennas are arranged in a staggered fashion across the elongate separation compartment 8 so that any two neighboring antennas from the same side and the closest antenna from the opposite side are in a triangular, more preferably substantially isocesceles, configuration. The antennas are further arranged, preferably, such that an antenna from any particular set is surrounded by antennas from the other sets. It is also preferred that the antennas be arranged to form a sequence of repeating patterns of electrical potential so that among the antennas of the same set, an antenna is about equal distant from its upstream and downstream neighbors along the elongate separation compartment. As can be seen in FIG. 1, antennas 12C, 12B' and 13A form a triangular configuration. Antennas 12A' ,and 13A', which have the same electrical potential, are equal distant from 13A, which is associated with the same electrical potential but of the opposite polarity.

Figure 2:
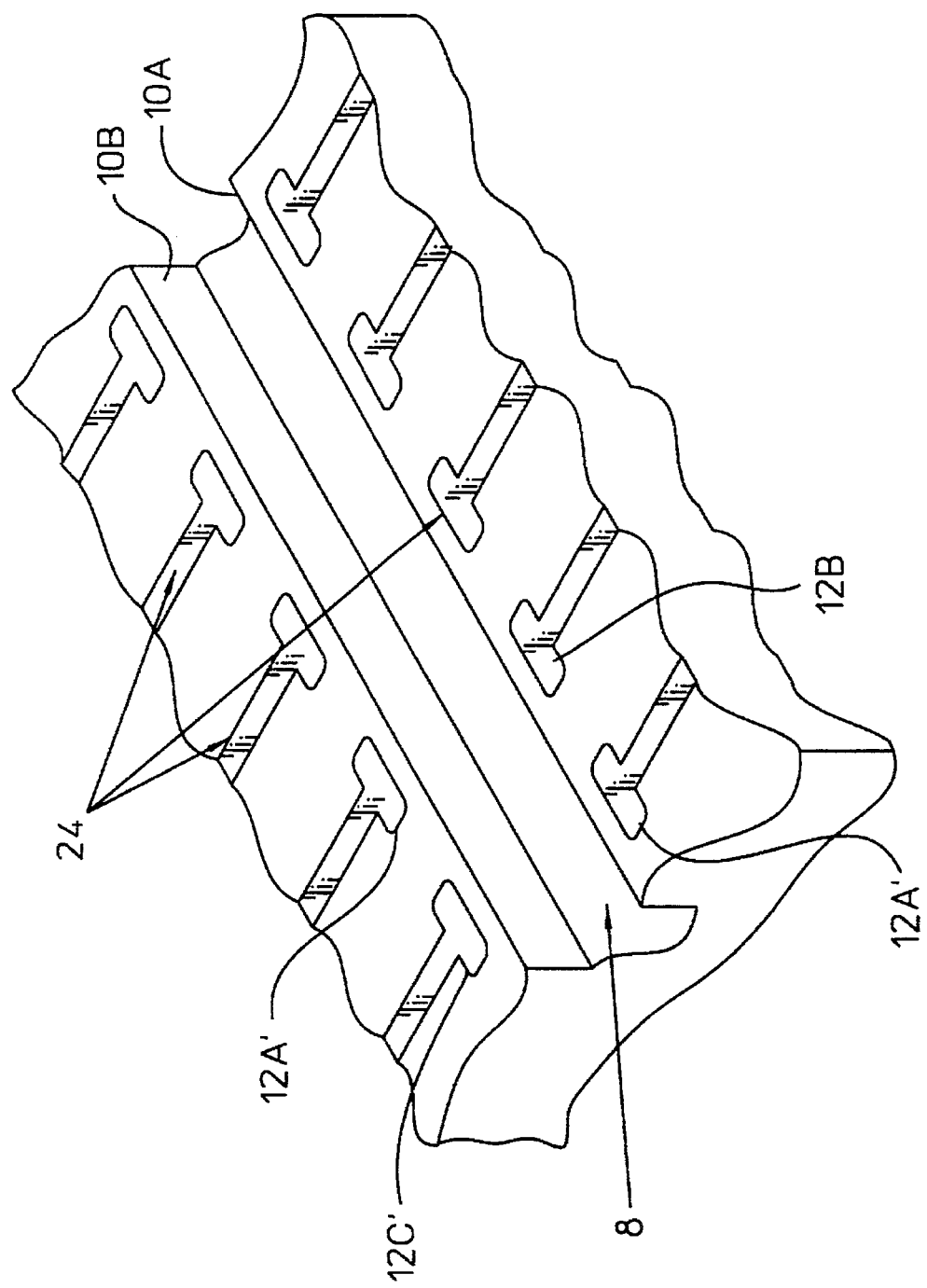
FIG. 2 is an isometric view in portion of a substrate of a miniaturized column device constructed in accordance with the present invention.

Referring to FIG. 2, which shows in isometric representation of a portion of the miniaturized column device (MCD) of FIG. 1, the antennas (e.g., 12A, 12C', 12B, etc.) each has a relatively flat face (not shown) facing the sides 10A, 10B of the separation compartment 8. Preferably, the face of the antenna facing the side of the separation compartment is located a short distance away from the separation compartment so that the antenna is not exposed to any medium in the separation compartment 8. That distance (or gap) between the antenna and the side of the separation compartment closest thereto is about 5 microns, which is the preferred size. However, the gap can be about 1 to 50 microns, preferably about 3 to 10 microns. The size of the gap is selected such that when the oscillating electrical potentials are applied to the antennas, electric fields of adequate strength are generated between the antennas to move charged target substances through the separation compartments at desired speeds.

Although elongate separation compartments of various sizes can be used in the present application, typically the opposing sides of the separation compartments are about 5 to 500 microns, preferably about 10 to 200 microns apart. To provide adequate electric fields for drawing target substances along the elongate separation compartment, the antennas are typically separated from its neighboring antenna on the same side of the separation compartment by a distance of about 1 micron to 500 microns, preferably 1 micron to 100 microns. Generally, the signal generators 22A, 22B, 22C, each applies to its respective antennas an oscillating electrical potential having a peak to peak voltage up to about 100 Volts (i.e., about between 0 Volt and 100 Volts), preferably about 0.1 Volt to 10 Volts. These voltage ranges, with the appropriate gap and antenna positions, will provide an electric field of about 3 to 3000 Volts per cm, preferably about 30 to 300 Volts per cm. For such a system, depending on the analytes, typically a separation compartment with a total length of about 1 mm to 100 mm, often about 1 mm to 50 mm, is adequate for analysis of target substances.

Figure 3:
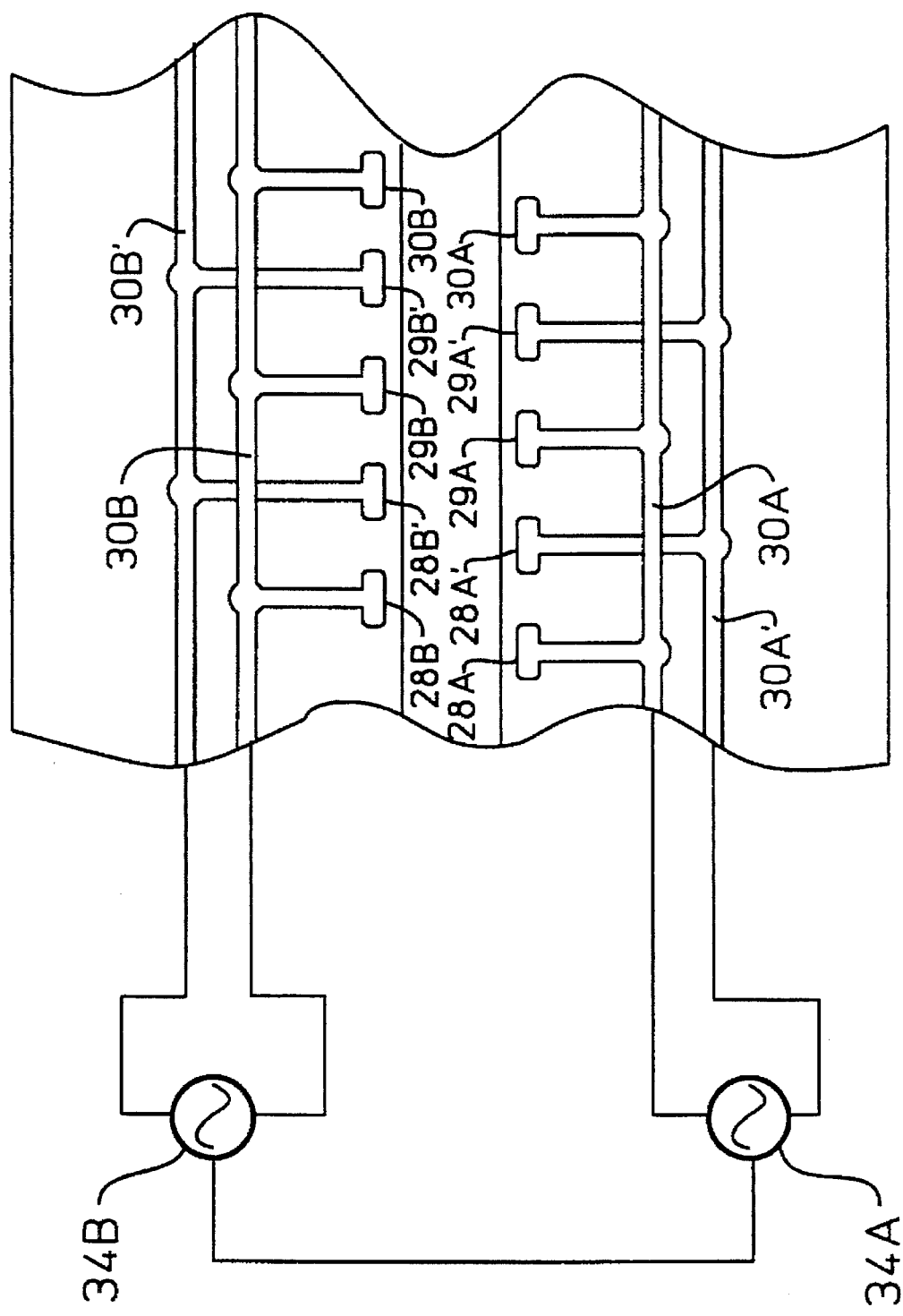
FIG. 3 is a schematic representation in portion of another embodiment of a miniaturized column analytical apparatus having a miniaturized column device constructed in accordance with the present invention.

Although an embodiment of the present invention having three sets of antennas associated with three different oscillating electrical potentials is shown in FIGS. 1 and 2, it is understood that other embodiments having various numbers of sets of antennas can be made and used in accordance with the present invention. To create a smooth transition of electric fields and yet not to result in undue complexity which may lead to manufacturing difficulty, preferably 2–6 sets, more preferably 3–5 sets of antennas are used in a MCD. For illustration, FIG. 3 shows an embodiment with two sets of antennas each associated with a different oscillating electrical potential. In this embodiment, antennas 28A, 29A, 30A, etc. are connected to electrical connector strip 30A. Antennas 28A', 29A', etc. are connected to electrical connector strip 30A'. Likewise, electrical connector strips 30B and 30B' are, respectively, connected to antennas 28B, 29B, 30B, etc. and 28B', 29B', etc. An oscillating signal generator 34A is connected at its two opposing poles to electrical connector strips 30A and 30A', respectively. Likewise, oscillating signal generator 34B is connected at its opposing poles to electrical connector strips 30B and 30B', respectively to provide two different oscillating electrical potentials to the two sets of antennas represented by A and B. Again, as in FIG. 1, the oscillating signal generators 34A and 34B in FIG. 3 are connected electrically so that the oscillating electrical potentials oscillates about a common (e.g., 0) electrical potential point.

Figure 4:
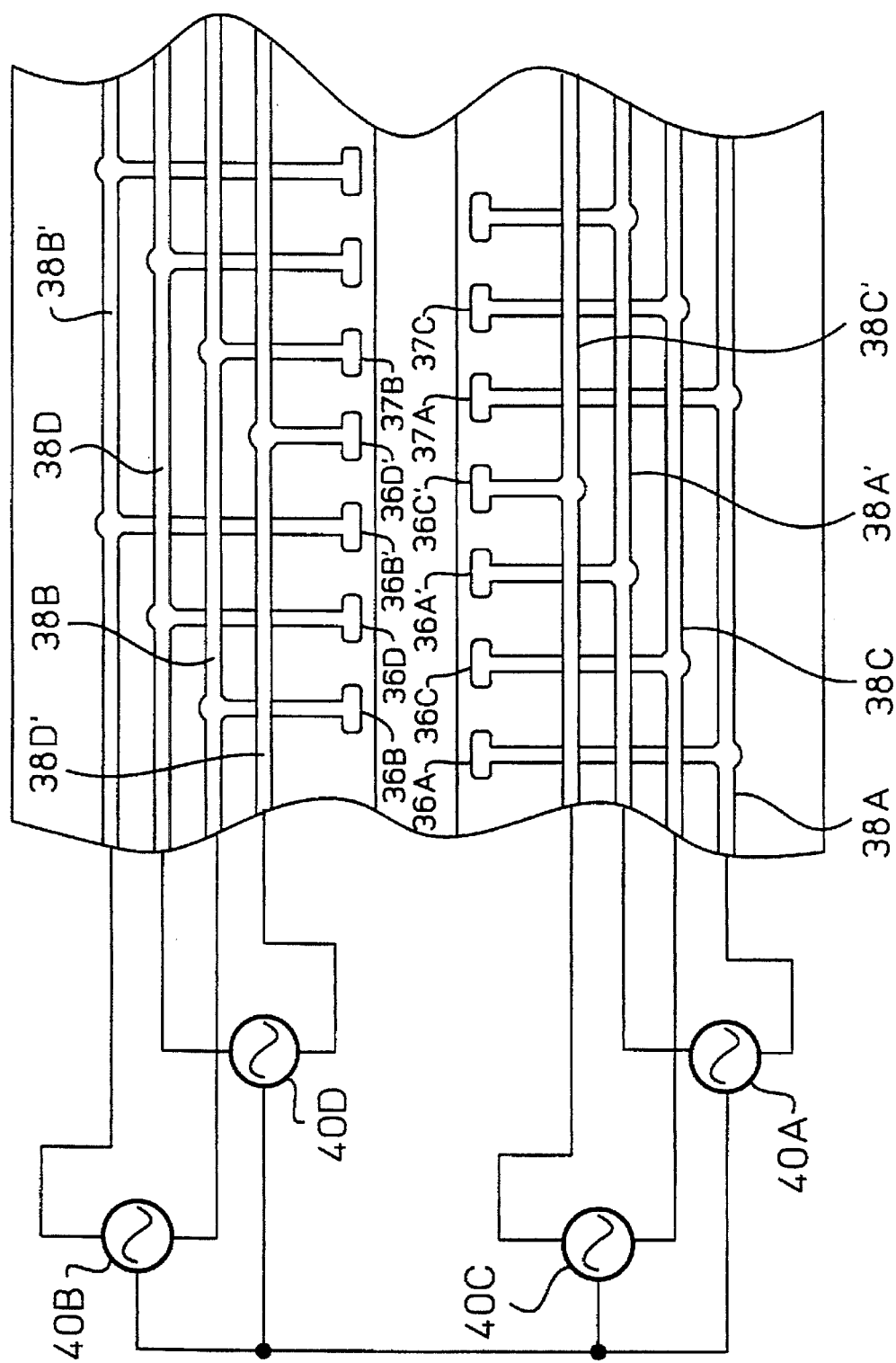
FIG. 4 is a schematic representation in portion of another embodiment of a miniaturized column analytical apparatus having a miniaturized column device constructed in accordance with the present invention.

As a further illustration of the present invention, FIG. 4 shows another embodiment wherein the MCD has 4 sets of antennas, each being associated with a different oscillating electrical potential. Among the antennas (36A, 36B, 36C, 36D, 36A', etc.) in FIG. 4, all antennas having the same letter are connected to an electrical connector strip with the same latter (such as 38A, 38B, 38C, 38D, 38A', etc.) which is associated with an oscillating electrical signal generator (e.g., 40A, 40B, 40C, 40D) of the same letter. Thus, each set of antenna is associated with an oscillating electrical potential distinct from the others.

Movement of Charged Particle in the Miniaturized Column Device

Figure 5:
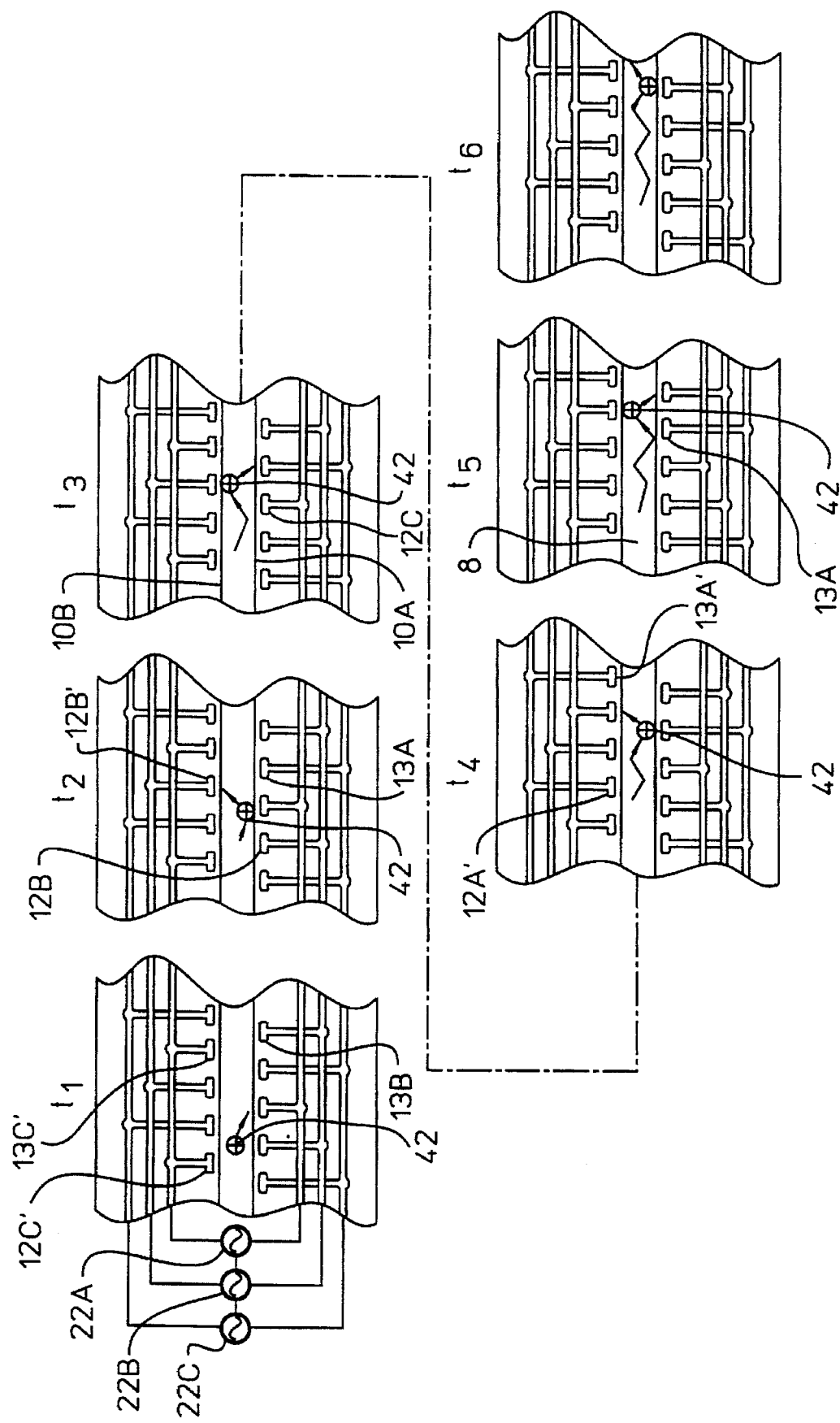
FIG. 5 is a schematic representation in portion showing the movement of a charge particle in the embodiment of FIG. 1 over time.

FIG. 5 shows a sequential representation of how a charge particle is moved along the elongate separation compartment according to the present invention by using an embodiment shown in FIGS. 1 and 2. However, it is understood that the application of the apparatuses of the present invention is not limited by any theory and a person skilled in the art will be able to use the present invention based on the disclosure.

Referring to FIG. 5, the separation compartment 8 has a medium through which dissolved, charged particles can propagate. Using liquid media, it is preferred to apply a surface treatment of the channel so as to eliminate irreversible adsorption of solutes to the substrate material. "Surface treatments" as used herein refer to preparation or modification of the surface of a microchannel which will be in contact with a sample during separation, whereby the separation characteristics of the device are altered or otherwise enhanced. Such treatments can include: physical surface adsorptions; covalent bonding of selected moieties to functional groups on the surface of microchannel substrates (such as to amine, hydroxyl or carboxylic acid groups on condensation polymers); methods of coating surfaces, including dynamic deactivation of channel surfaces (such as by adding surfactants to media), polymer grafting to the surface of channel substrates (such as polystyrene or divinyl-benzene) and thin-film deposition of materials such as diamond or sapphire to microchannel substrates. Such treatment techniques are known in the art. Additionally, the separation compartment may be filled with an anticonvective medium such as beads, gel, and the like.

When the apparatus is properly operated, the charged target substance particle 42 is first moved towards an antenna proximate and downstream thereto. As the oscillating signal generators oscillate, the electrical potentials of the antennas vary according to the oscillation of the signal generators 22A, 22B, 22C. The electrical potential of the antennas varies in such a way that the antenna upstream and proximate to the charged target substance particle has an electrical potential that is attractive to the target substance while the antenna downstream and proximate to the target substance particle has an electrical potential that is repulsive to the target substance particle. In this way, the target substance particle 42 migrates in a generally zig zag manner along the elongate separation compartment. By such zig zag movements between antennas at opposing sides of the elongate separation compartment, the target substance particle travels a tortuous path generally in the central region, rather than having a bias to only one side towards the surface of the microchannel, along the separation compartment.

Figure 6:
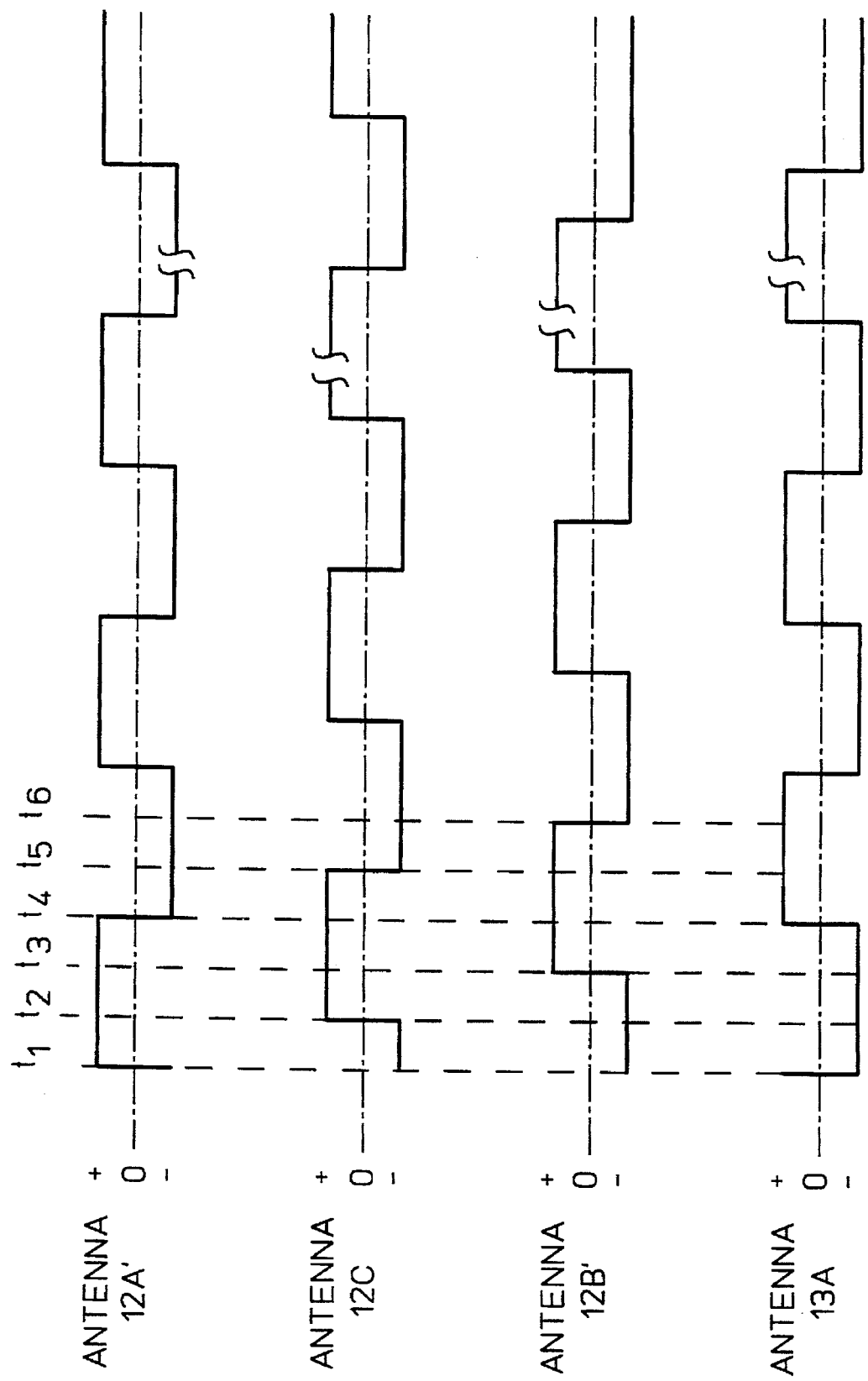
FIG. 6 is a representation of the oscillation of electrical potentials of selected antennas in the embodiment of FIG. 1.

FIG. 6 depicts the temporal variation of the electrical potential at antennas 12A', 12C, 12B', and 13A. In the embodiment shown in FIG. 6, the signal generators 20A, 20B, 20C apply oscillating signals having a square wave form to the antennas. Although square wave signals are used in this embodiment, other regular waveforms, e.g., sinusoidal, sawtooth, and the like, can be use. The square wave oscillates about a 0 (zero) voltage (or center) point, which is common for all the antennas. Typically, the 0 voltage point is the electrical potential of a reservoir of a buffer that is in fluid communication with the separation compartment 8. Referring to FIGS. 5 and 6, considering a target substance particle having a positive net electrical charge to be located at time=$t_1$ (as shown in FIG. 5) between antennas 12A' and 12B, the particle 42 is repelled by antennas 12C', 12B, and 12A'. On the other hand, it is attracted towards antennas 12C, 12B', and 13A. Therefore, there is a net electrical motive force moving the particle 42 downstream. However, because the attractive antenna closest to particle 42 is antenna 12C, particle 42 moves towards the side 10A of the separation compartment.

At time=$t_2$ antenna 12C changes polarity and becomes repulsive to particle 42. Because at this point the polarities of the neighboring antennas remain unchanged, particle 42 is repelled by antennas 12B, 12A' and 12C while being attracted towards antennas 12B', 13A, and 12C'. Again, there is a net electrical motive force moving the particle 42 downstream. However, the attractive antenna closest to the particle 42 is now antenna 12B'. As a result, particle 42 moves toward antenna 12B' away from antenna 12C.

AT time=$t_3$, antenna 12B' changes polarity and becomes repulsive to particle 42. Particle 42 therefore moves away from antenna 12B' towards antenna 13A. Likewise, antenna 13A changes polarity at time=$t_4$, antenna 13C' changes polarity at time=$t_5$, and antenna 13B changes polarity at time=$t_6$. In each case, the antenna proximate particle 42 changes polarity and repels the particle to the opposite side of the separation compartment 8. As a result, particle 42 travels downstream in the separation compartment in a zig zag manner.

Figure 7:
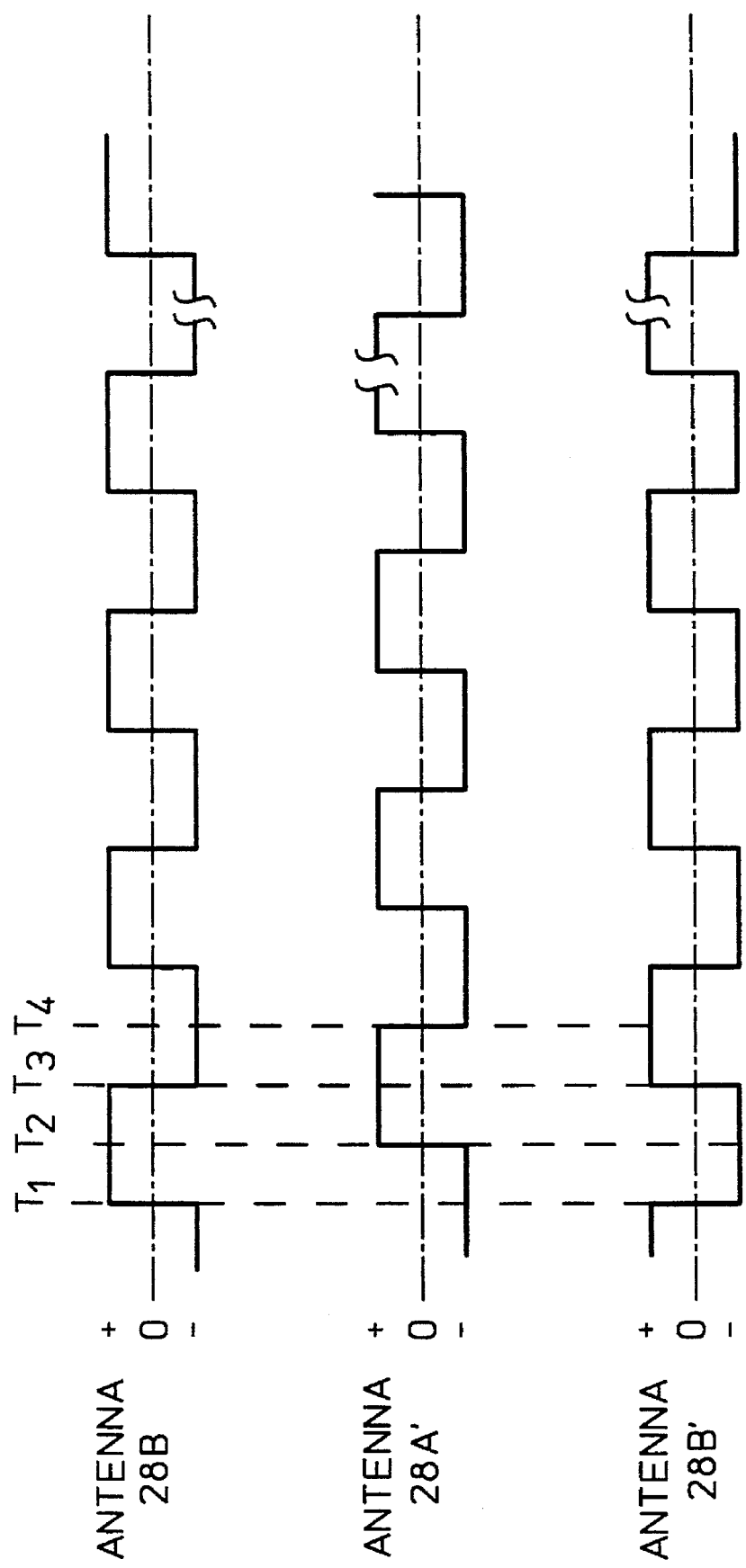
FIG. 7 is a representation of the oscillation of electrical potentials of selected antennas in the embodiment of FIG. 3.

Likewise, a target substance particle can be moved along the separation compartment of a MCD having two different sets of antennas as shown in FIG. 3. FIG. 7 shows an illustrative square wave form for such a MCD over time.

Again, for illustrative purpose, consider a target substance particle with a net positive charge located proximate to antenna 28B. At time=$T_1$, antenna 28B reverses polarity, acquiring a positive electrical potential relative to the 0 voltage point in the MCD. Thus, antenna 28B becomes repulsive to the particle. At the same time, antenna 28A, the antenna that is upstream on the opposing side of the separation compartment, remains repulsive to the particle. On the other hand, downstream of the particle, antenna 28A' has a negative electrical potential and antenna 28B' also changes polarity to attain a negative electrical potential. Thus, the two antennas closest to and upstream of the particle are attractive to the particle. Therefore, there is a net electrical motive force moving the particle downstream in the separation compartment. Furthermore, in a normally operated system, a medium in the separation compartment moves downstream. The moving medium, as well as the particle itself, has a momentum. Such momenta facilitate the downstream movement of the particle when it is in a location at which the electrically derived driving force (the sum of the attractive and the repulsive forces) upstream and downstream to the particles is at a minimum.

AT time=$T_2$, the particle would have attained a position proximate antenna 28A'. As antenna 28A' changes polarity and becomes repulsive to the positively charged particle, it moves the particle downstream and across the separation compartment to the opposing side. Likewise, At time=$T_3$ and time=$T_4$, respectively, antennas 28B' and 29A reverse polarity and repell the particle. In this manner, the particle is moved downstream by the electric fields generated by the oscillating antennas downstream in a zig zag fashion.

MCDs with other numbers of sets (different than 2 and 3) of antennas having different oscillating electrical potentials will also move target substance particles downstream along a separation compartment in a manner similar to that described above.

In electrophoresis, different target substances are separated based on different velocities as the target substances moved through the elongate separtion compartment. The velocity, $V_{cp}$, of a charged particle in a medium in an electric field is related to the electrophoretic mobility of the charged particle:

$$\mu_{epm} = V_{ep}/E \qquad (1)$$

The electrophoretic mobility, $\mu_{epm}$, is dependent on the net charge of the particle, the vescosity of the medium in which the particle moves and a size-shape factor, r, of the particle:

$$\mu_{epm} = \frac{nZ}{4\pi\eta r} \qquad (2)$$

where nZ is the total net charge of the particle, $\eta$ is the viscosity of the medium, and r is the size-shape factor.

When an electrical potential exist between two conductors separated by a nonelectrically conducting substance, an electric field is generated between the two conductors. That electric field will tend to move a charged particle from one conductor to the other, in a manner similar to that described for the positively charged particle 42 between e.g. antennas 12A' and 12C.

Figure 8:
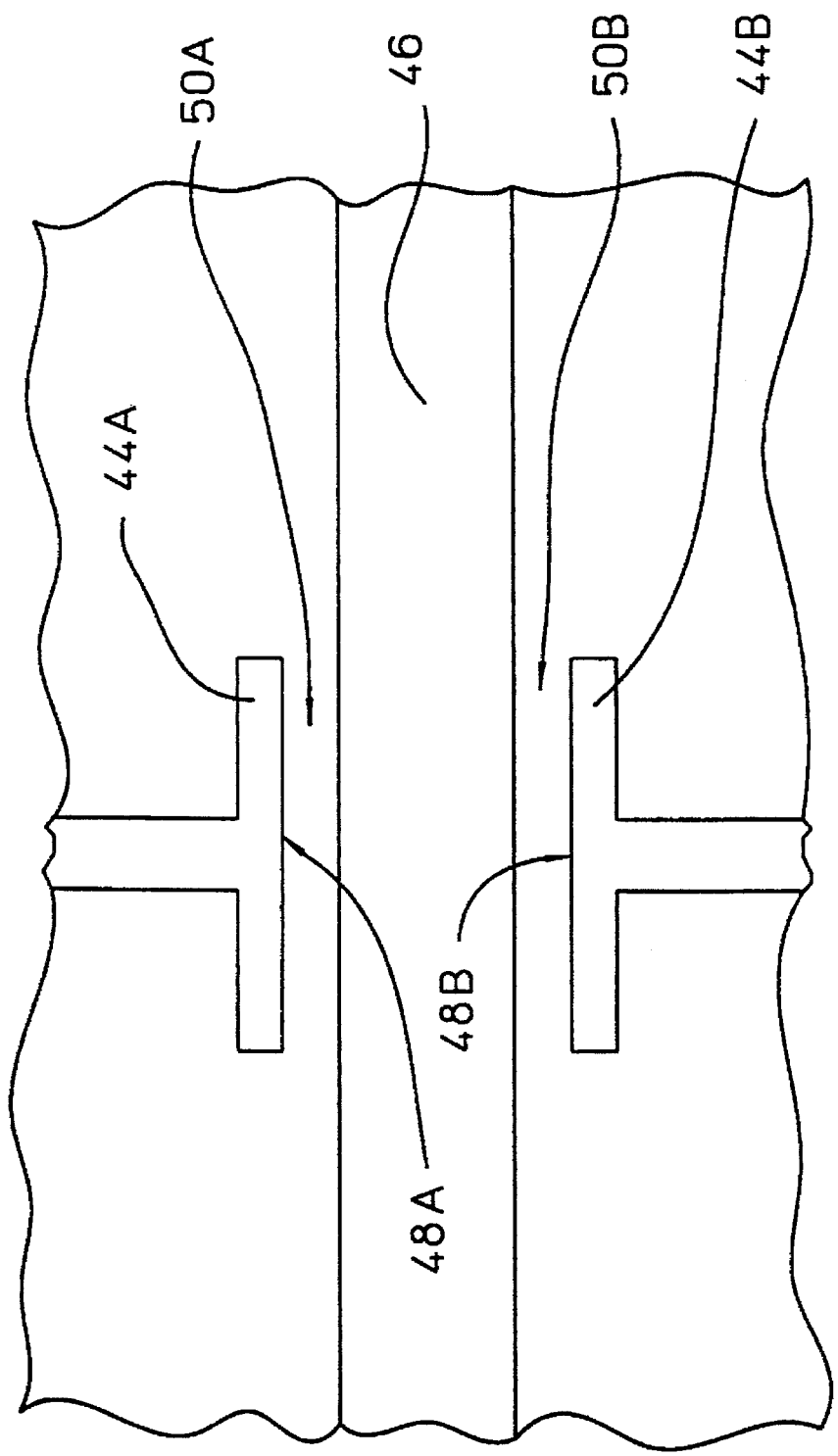
FIG. 8 is a representation of a portion of another embodiment of a miniaturized column device of the present invention to illustrate capacitance effect.

For clarity of description, consider, for example, a portion of a MCD with two antennas 44A, 44B on the two sides of a separation compartment 46 as shown in FIG. 8. Antennas 44A, 44B each has a surface (48A, 48B respectively) with the same area, A, facing each other. Antennas 44A, 44B are each separated from the proximate side of the separation compartment 46 by a gap (50A, 50B respectively).

The capacitance, C, of a nonconductive material, m, of thickness, d, and area A is:

$$C_m = \kappa_m \epsilon_o A/d_m \qquad (3)$$

wherein $\kappa$ is the dielectric constant of the material, $\epsilon_o$ is the permittivity constant and the subscript m signifies the material described by the variable associated with tht subscript. $\epsilon_o$ is $8.854 \times 10^{12}$(ampere.second)/(volt.meter).

If C is the capacitance of the gap 50A, $C_2$ is the capacitance of the medium between the antennas 44A, 44B, and $C_3$ is the capacitance of the gap 50B, each relating to the same surface area A, the overall capacitance, $C_\Sigma$ between the antennas 44A, 44B is thus:

$$C_\Sigma = \frac{1}{\frac{1}{C_1} + \frac{1}{C_2} + \frac{1}{C_3}} \qquad (4)$$

Assuming the gap is made of polyimide and the medium in the separation compartment is water, the dielectric constants for the gap and for water, are 8 respectively. Assuming each of gaps 50A, 50B is 5 μm thick, the water between the opposing sides of the separation compartment is 100 μm thick, and area A is 100 μm×50 μm substituting these values into equations (3) and (4).

$$C_1 = C_2 = C_3 = 35 \text{ fF} \qquad (5)$$

Because of the capacitance between the antennas on opposing sides of a separation compartment, if a DC voltage source is applied to two such antennas, the antennas will act as a capacitor and become charged. Even if the DC voltage source is turned off, electrical charges have to be removed or added to an antenna to allow it to change the polarity and magnitufe, thereby changing its attractive or repulsive effect on a charge particle. If the antennas are in contact with a medium that has ions or charged particles, the antennas may slowly lose their charge after the DC voltage source is turned off. As previously stated, in the present invention, the antennas are not in contact with the medium. However, since the antennas are connected to oscillating voltage sources, they can quickly charged and discharged to result in the desired electric fields for moving the charged target substance particle downstream towards the exit end.

In the space between two infinite field pads (or antennas) separated by a distance, d, and having an electrical potential difference, U, the electric field is:

$$E = U/d$$

Such an electric field will exert a force on a charged particle to move it from one antenna to the other with the direction of movement being dependent on the polarities of the charge and the antennas.

In the present invention, the electrical potentials of the antennas periodically change in polarity. The antennas, due to their diffences in electrical potentials, produce a plurality of electric fields along the separation compartment. In certain cases (such as when sinusoidal or saw-tooth waveforms are used), the magnitudes of the electrical potentials also change periodically. Because of the spatially repeating pattern of the antennas, the electric fields are spatially repetitive. In other words, the pattern of electric fields in one portion of the separation compartment is present at regular spatial intervals along the elongate separation compartment. Also, because the antennas have oscillating electrical potentials, a temporally repetitive pattern of electric field results as well. Thus, the pattern of electric field along the separate compartment repeats itself with every period of oscillation and thus is "oscillating." Because the electric fields move not only in the downstream direction, but also in the generally lateral (i.e. perpendicular to the downstream direction) with time, the resulting electric fields along the elongate separation compartment can be considered to "wander" in a regular, predictable pattern along the separatent compartment.

The antennas and the variation of electrical potentials of the antennas are arranged such that the plurality of electric fields oscillate and wander in a way to move charge particles downstream. This is accomplished by varying the electrical potential to result in a net motive force directed downstream at certain locations along the separation component at regular temporal and spatial intervals. As previously described, preferably, the antennas are evenly spaced apart along the separation compartment. Different sets of antennas have the same frequency but different phases of oscillation. It is also peferred that the electrical potential of an antenna differs from its neighboring antenna on the same side of the separation compartment by 360°/n, wherein n is the number of sets of antennas associated with different electrical potentials. Preferably, the electrical potential of an antenna leads that of an antenna that is closest to it and on the opposing side of the separation compartment by a phase difference of 180°/n.

Although it is not necessary to oscillate all of the antennas simultaneously, simultaneous oscillation is preferred becuase it obviates sofisticated control systems to sequentially activate (i.e., oscillate) the antennas. Such sequential activation can be done, for example, by sequentially activating the antennas for a set time period such that a block of a given number of activated antennas moves progressively down the separation compartment with time.

Because every antenna with a positive electrical potential has a corresponding antenna with a negative potential, at any given moment, half of the antennas are attractive and half of the antennas are repulsive to a particular charged particle. Along the separation compartment, certain locations will render a net downstream directing electrical motive force and certain locations will do the opposite to a charged particle. Therefore, the spatial and temporal variation of the electric fields need to be coordinated (or orchastrated) so that a charged particle traverses a distance to receive the correct net motive force when the antennas change polarity. Otherwise, if a charge particle does not move fast enough to keep up with the wandering electric fields, it may fall into a region where the net motive force is directed upstream. This is analogous to a surfer having to stay on a wave (of oscillating water molecules) in order to be carried forward at maximum speed.

As previously described, the velocity of a charged particle moving through an electric field is dependent on its electrophoretic mobility. To analyze a charged target substance in a MCD of the present invention, after a sample suspected of containing a charged target substance has been introduced into the inlet end of the separation compartment of the MCD, the oscillation is tuned through a range of frequencies (preferably, from high frequency to low frequency) to achieve an optimal frequency (or "resonant" frequency) for moving the charged target substance. This can be accomplished, for example, by obtaining a table of correlation of frequencies and substances of interest. Such a table can be established by introducing one known target substance at a time into the MCD and tuning the frequency of oscillation until the target substance is detected at the exit end of the separation compartment. Generally, based on the elongate dimension of the separtion compartment, the arrangement of the antennas, and the frequency of oscillation, the time needed for a "resonant" target substance to traverse the elongate separation compartment can be estimated.

When such a table is available, a sample containing unknown substances can be introduced into the MCD and the oscillation can be ramped (i.e., varied in a gradual manner) through a range of specific frequencies so that the frequencies and the time periods needed for the components of the sample to traverse the separation compartment can be determined. These data will show the identity of the unknown substances. The range of frequencies used depends on the type of molecules to be analyzed and the design of the MCD (such as spacing of the antennas, and electric field strength). Typically, the range of frequency is about 10 Hz to 0.1 MHz. For example, for macromolecules such as proteins, DNA fragments, and the like, the range is preferably 500 Hz to 3 kHz.

Making a Miniaturized Column Device

The miniaturized column devices (MCDs) of the present invention can be made by forming (or micromachining) microstructures such as microchannels and depressions, as well as electrical components such as antennas and electrical connectors, on a substrate and arranging a cover member on the substrate to form a body of the MCD. The cover member can be a cover plate which in conjuction with a microchannel of the substrate defines the separation compartment. The cover member can also be another substrate with microstructures with or without components so that the two substrates act as two halves that form a body when becoming attached in alignment. The microchannels of the two halves can define the separation compartment.

Depending on the substrate and the technique chosen, the electrical components can be formed on a substrate before or after the formation of microstructures such as microchannels. For example, a substrate can be masked to expose selected areas and sputtered with a metal. After removing the mask, electroplating can then be used to build up the thickness of the metal pattern on the substrate to form the antennas, electrical connectors, and the like. Microstructures such as microchannels can then be formed on the substrate by techniques such as etching, laser ablation, and the like. The substrate can then be processed (e.g., by laser ablation or etching) to obtain the microstructures.

As an alternative, the microstructures can be formed on the substrate before the electrical components. For example, a silicon substrate can be processed to form the microstructures. The electrical components can then be deposited on the substrates by, for example, metal sputtering followed by electroplating.

Another alternative is to bond a thin metal layer to a substrate and form the electrical components (such as antennas) and the microstructures. Selected portions of the metal layer can be etched away chemically. In the exposed area, the substrate can be further processed to obtain the microstructures.

Substrates such as polymers, glass, silicon, silicon dioxide, quartz, ceramics, and the like are comtemplated as suitable substrates in the present invention. Metals such as copper, silver, aluminum, nickel, and other metals commonly used for electrical conductors can be used for the electrical components such as antennas and electrical connectors.

Figure 9:
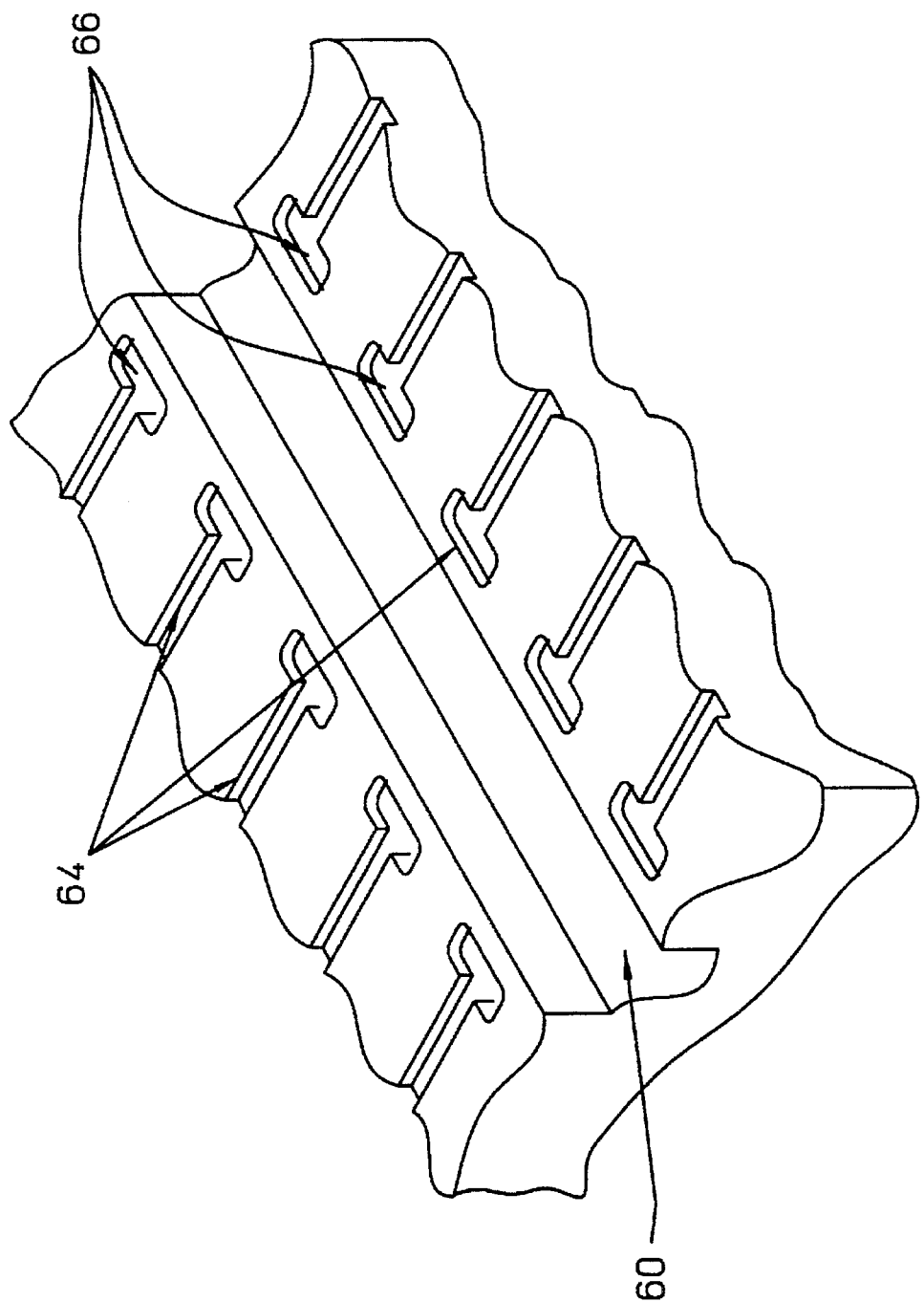
FIG. 9 is a representation in portion of a substrate laser-ablated to obtain microstructures according to the present invention.

To illustrate an example of such a process, referring to FIG. 9, a portion of a slab shaped polyimide substrate 60 with a microchannel, depressions 66 for receiving metal to form antennas, and grooves (or slots) 64 for receiving metal to form bridges that connect to electrical connectors are shown (while the grooves for the electrical connectors are not shown). The depressions 66 are each separated from the channel by a thin layer of substrate material so as not to be in communication with the channel 60. The microstructures (depressions, grooves, depressions) are formed by micromachining (e.g., laser ablation, as deccribed below). A thin layer of copper is then sputtered over a mask into the grooves 64, depressions 66, and the electrical connectors (not shown) to a thickness of about 1 micron. Electroplating is then used to build up the sputtered copper layer to about to 10–15 microns thick by electroplating. Then a polyimide coating can be applied on top of the substrate to fill the remaining space in the gooves 64 and the depressions 66 to seal the metal as well as to provide a more evenly level surface. This coating can be thin compared to the dimensions of the microchannel. A cover member can then be applied on top of the substrate to form the body of the MCD. If desired, the microchannel can be further laser ablated to refine the dimensions. A variation of this method is to form the electrical components first and laser ablate the microchannel afterward.

Another example is to mask and etch a laminate of polyimide and copper to obtain the antenna and electrical connectors on the laminate. On the other side (the polyimide side), a microchannel formed by laser ablation. Then another laminate is similarly processed so that two similar halves are formed. The two halves are then bonded together so that the microchannels face and unit with each other to form a separation compartment. This technique has the advantage of being applicable in making antennas of a wide range of surface area and the antennas can be made to face the same direction as the planar surface of the laminate. Furthermore, this process can be combined with a process similar to that of FIG. 9. In this way, antennas can be formed with antennas on two sides or four sides of a four sided (for example, with rectangular cross section) separation compartment.

It is to be understood that microstructures and electrical components of various size and shapes can be formed in an analogous manner with a variety of micromachining techniques. Although a substrate with a slab shape is described in the embodiments shown in the figures, based on this disclosure, one skilled in the art will be able to construct miniaturized column devices with other shapes. Likewise, micromaching techniques (such as etching), in addition to laser ablation, are also application.

Formation of Microstructures on Substrate

As stated above, a variety of techniques can be used to form (or micromachine) microstructures (e.g., microchannels and holes), as well as larger structures (e.g., chambers and reservoirs) on the body of the miniaturized column device of the present invention. Such techniques include, but are not limited to, dry etching, chemical etching, LIGA, and laser ablation. Depending on the techniques selected, the appropriate microstructures can be formed in a suitable substrate either before or after the formation of the necessary electrical components on the substrate.

The term "LIGA process" is used to refer to a process for fabricating microstructures having high aspect ratios and increased structural precision using synchrotron radiation lithography, galvanoforming, and plastic molding. Under a LIGA process, radiation sensitive plastics are lithographically irradiated at high energy radiation using a synchrotron source to create desired microstructures (such as channels, ports, apertures and micro-alignment means), thereby forming a primary template. The primary template is then filled with a metal by electrodeposition techniques. The metal structure thus formed comprises a mold insert for the fabrication of secondary plastic templates which take the place of the primary template. In this manner highly accurate replicas of the original microstructures may be formed in a variety of substrates using injection or reactive injection molding techniques. The LIGA process has been described by Becker, E. W., et al., *Microelectric Engineering* 4(1986) pp. 35–56. Descriptions of numerous polymer substrates which may be injection molded using LIGA templates, and which are suitable substrates in the practice of the subject invention, may be found in "Contemporary Polymer Chemistry", Allcock, H. R. and Lampe, F. W. (Prentice-Hall, Inc.) New Jersey (1981).

Chemical etching is an alternative way of forming microstructures on a substrate and such techniques are known in the art. For example, a layer of photosensitive polymer (e.g., polyimide) can be covered with a mask and exposed to UV light to cross-link the polymer. The layer is then etched with a suitable chemical to removed polymer from selected areas according to the pattern of the mask. This results in structures such as channels and depressions on the layer. An example of a dry technique for etching polymers is a plasma based process. In this process, a mask is layered over a polymeric layer and ionized gases is directed to the polymeric layer to erode the area not covered by the mask. Etching techniques, including wet or dry processes, for polymeric substances are described, for example, in Frazier, A. B., et al., *Sensors and Actuators A*, 45:47–55 (1994) and references cited therein.

For glass, quartz, silicon, and silicon dioxide substrates, etching techniques are also practicable. Generally, such a technique involves steps of masking and etching with chemical. For example, a silicon substrate is first covered with a coating of silicon dioxide by thermal oxide deposition and then further coated with a photoresist. The photoresist is then masked and exposed to light of suitable wavelength by photolithography. By developing the photoresist, selected areas of the silicon dioxide is exposed. This exposed area is then etched chemically to remove the silicon dioxide, thus exposing a selected area of the silicon. This exposed silicon area can then be chemically etched to form grooves, depressions, and the like. Along the way, the photoresist and the silicon dioxide coatings can be removed. By using analogous methods, glass and silicon dioxide substrates can be masked and etched to result in microstructures on a substrate. Examples of such techniques can be found in, for example, Fan, Z. H., et al., *Anal Chem.*, 66(1):177–184 (1994), Manz et at., *Adv. in Chrom.* 33:1–66 (1993), and Manz et al., *Trends Anal Chem.* 10(5):144–149 (1991).

Laser Ablation of Substrate

A technique that is particularly suitable for forming microstures for a MCD of the present invention is laser ablation. The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type. It is understood that various parameters related to the operation of the laser, such as the intensity, the angle of incidence of the laser light beam on the substrate, and the duration of exposure can be varied to achieve the specific profile of the microstrucures desired.

The term "substrate" is used herein to refer to any material which is processed to have microstructures and electrical components formed thereon. Although, in the following illustrative description, microstructures are formed on a polymeric substrate, laser ablation can be used for forming similar structures in ceramics (including aluminum oxides and the like), silicon containing materials (e.g., silicon, glass, silicon dioxide), and the like.

In general, any substrate which is laser light (e.g., UV) absorbing provides a suitable substrate in which one may laser ablate features. Accordingly, under the present invention, microstructures of selected configurations can be formed by imaging a lithographic mask onto a suitable substrate, such as a polymer or ceramic material, and then laser ablating the substrate with laser light in areas that are unprotected by the lithographic mask.

In laser ablation, short pulses of intense laser (e.g., ultraviolet) light are absorbed in a thin surface layer of material within about 1 µm or less of the surface. Preferred pulse energies are greater than about 100 millijoules per square centimeter and pulse durations are shorter than about 1 microsecond. Under these conditions, the intense light photo-dissociates the chemical bonds in the material. Furthermore, the absorbed energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other ultraviolet light sources with substantially the same optical wavelength and energy density may be used to accomplish the ablation process. Preferably, the wavelength of such light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins, T. A., et al., *Laser Focus Electro Optics*, (1987) pp. 54–70; U.S. Pat. Nos. 5,291,226 and 5,305,015 to Schantz et al.

Microstructures such as microchannels, depressions, grooves, and the like can be formed in a planar substrate by excimer laser ablation. Other lasers such as a frequency multiplied YAG laser may also be used in place of the excimer laser. In such a case, a complex microstructure pattern useful for practicing the invention may be formed on a suitable substrate by combining a masking process with a laser ablation means, such as in a step-and-repeat process, where such processes would be readily understood by one of ordinary skill in the art.

In the practice of the invention, a preferred substrate comprises a polyimide material such as those available under the trademarks KAPTON or UPILEX from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof. Further, the polymer material selected may be produced in long strips on a reel, and, optional sprocket holes along the sides of the material may be provided to accurately and securely transport the substrate through a step-and-repeat process.

In the invention, the selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), micro-alignment means and separation chambers.

Alternatively, patterns such as the aperture pattern, the separation channel pattern, etc., may be placed side by side on a common mask substrate which is substantially larger than the laser beam. Such patterns may then be moved sequentially into the beam. In other contemplated production methods, one or more masks may be used to form apertures through the substrate, and another mask and laser energy level (and/or number of laser shots) may be used to define separation channels which are only formed through a portion of the thickness of the substrate. The masking material used in such masks will preferably be highly reflecting at the laser wavelength, consisting of, for example, a multilayer dielectric material or a metal such as aluminum.

The laser ablation system employed in the invention generally includes beam delivery optics, alignment optics, a high precision and high speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

Laser ablation may be used to form miniaturized separation channels and apertures in a wide variety of geometries. Laser-ablated channels or chambers produced according to the invention are easily fabricated having ratios of channel depth to channel width which are much greater than previously possible using etching techniques such as silicon micromachining. Such aspect ratios can easily exceed unity, and may even reach to 10.

Channels of a variety of cross sections (such as semi-circular, square, rectangular, trapezoidal shapes) can be formed. In a preferred embodiment of the invention, channels of a semi-circular cross section are laser ablated by controlling exposure intensity or by making multiple exposures with the beam being reoriented between each exposure. Accordingly, when a corresponding semi-circular channel is aligned with a channel thus formed, a separation chamber of highly symmetrical circular cross-section is defined which may be desirable for enhanced fluid flow through the separation device.

As a final step in laser ablation processes contemplated by the invention, a cleaning step is performed wherein the laser-ablated portion of the substrate is positioned under a cleaning station. At the cleaning station, debris from the laser ablation are removed according to standard industry practice.

Figure 10:
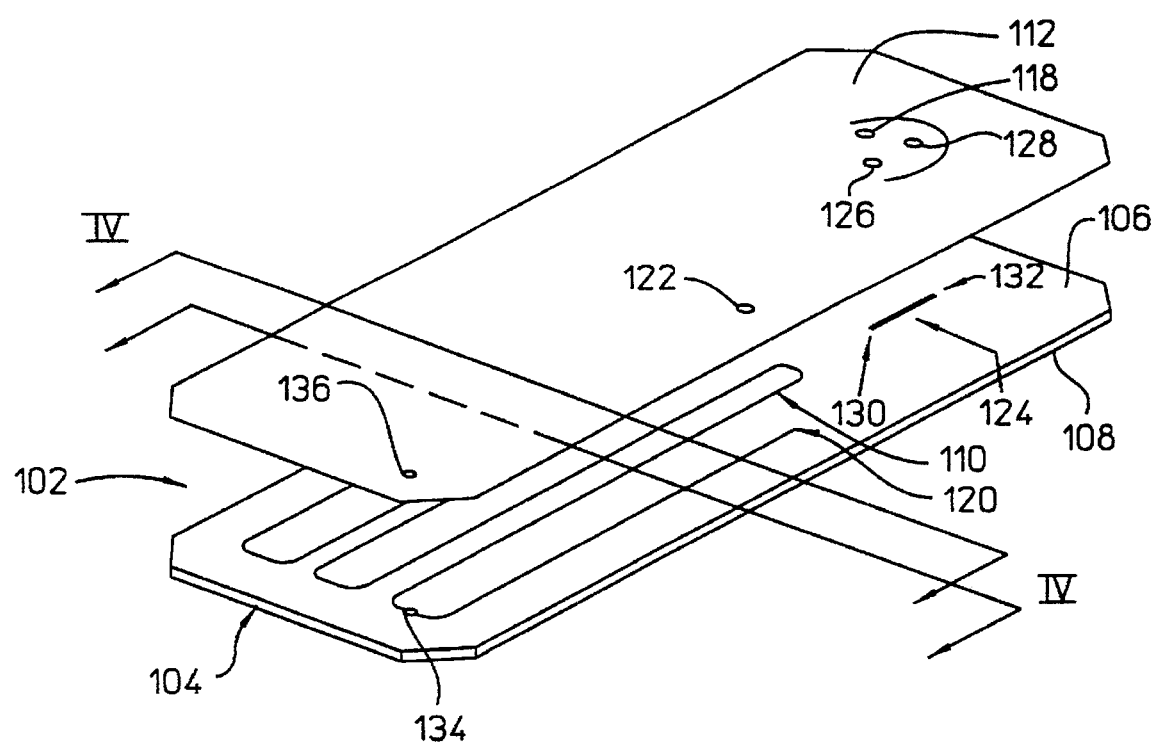
FIG. 10 is an exploded view of a miniaturized column device constructed in accordance with the present invention (with the electrical components being omitted for clarity purposes)

As will be appreciated by those working in the field of liquid phase analysis devices, the above-described method may be used to produce a wide variety of miniaturized devices. One such device is represented in FIG. 10 where a particular embodiment of a miniaturized column device is generally indicated at 102. In the figures related to this embodiment, for the sake of clarity of description, the electrical components (such as antennas, electrical connectors, etc.) are not shown or described. However, it is understood that one skilled in the art will be able to incorporate such electrical components in the device based on the present disclosure.

Generally, miniaturized column 102 is formed in a selected substrate 104 using laser ablation techniques. The substrate 104 generally comprises first and second substantially planar opposing surfaces indicated at 106 and 108 respectively, and is selected from a laser light material. As previously stated, examples of suitable substrates include ceramics and polymers such as (but are not limited to) polyimides, polyamides, polyesters, and polycarbonates.

In a particular embodiment of the invention, the miniaturized column device 102 comprises a column structure ablated on a chip, which, in the practice of the invention may be a machinable form of the plastic polyimide such as VESPEL. It is particularly contemplated in the invention to use such a polyimide substrate as, based on considerable experience with the shortcomings of fused silica and research into alternatives thereof, polyimides have proved to be a highly desirable substrate material for the analysis portion of a liquid phase separation system.

Figure 11:
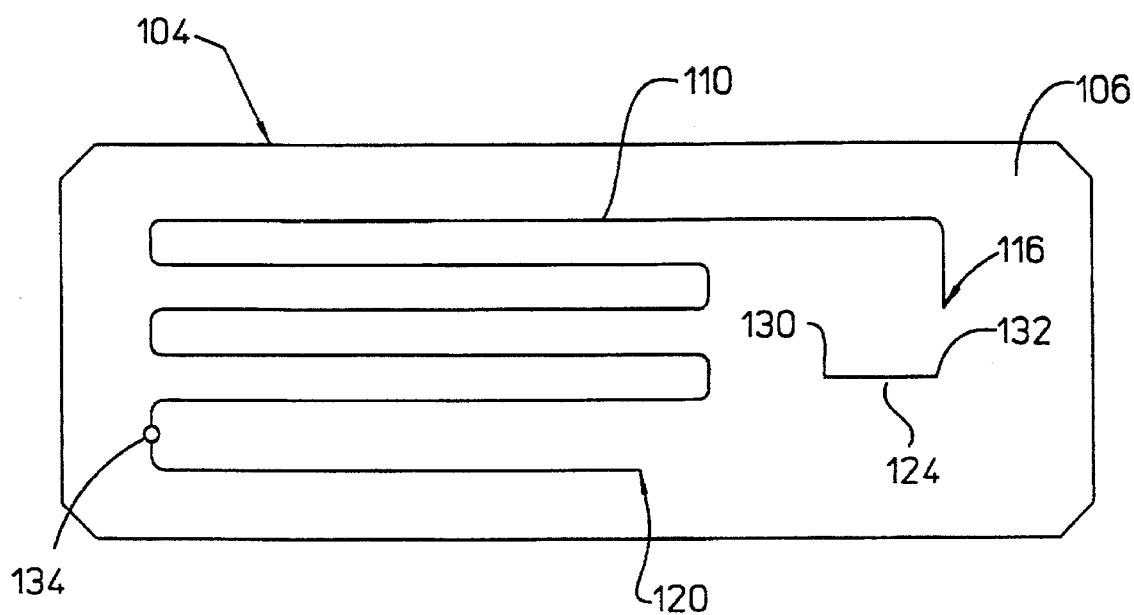
FIG. 11 is a plan view of the interior surface of the miniaturized column device of FIG. 10.
Figure 12:
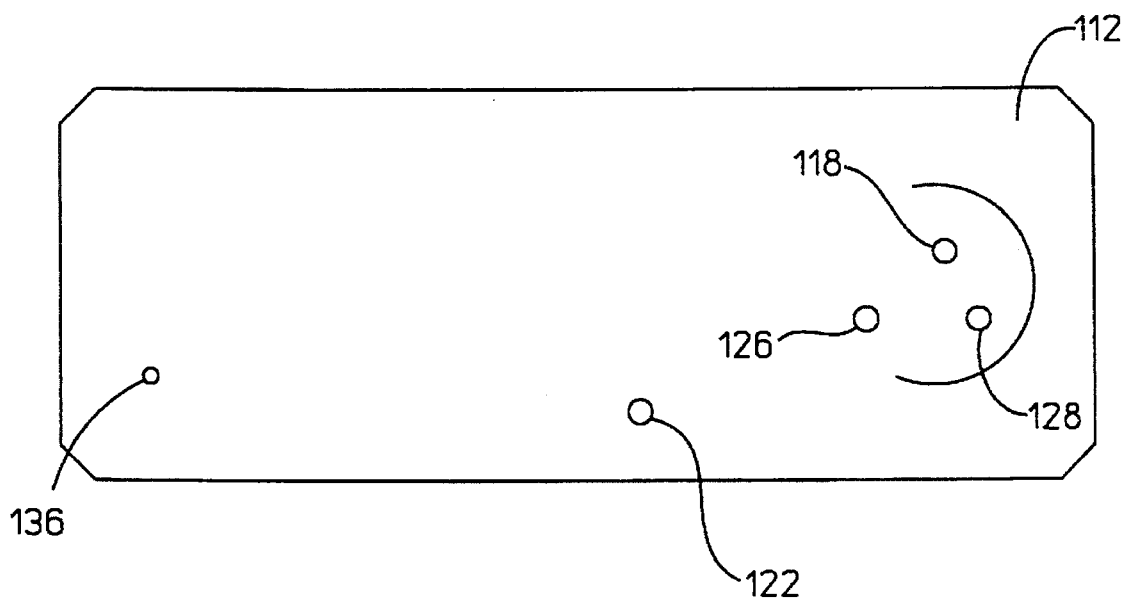
FIG. 12 is a plan view of the exterior surface of the device of FIG. 10.

Referring now to FIGS. 10–12, the substrate 104 has a microchannel 110 laser-ablated in a first planar surface 106. It will be readily appreciated that, although the microchannel 110 has been represented in a generally extended form, microchannels formed under the invention may be ablated in a large variety of configurations, such as in a straight, serpentine, spiral, or any tortuous path desired. Further, as described in greater detail above, the microchannel 110 may be formed in a wide variety of channel geometries including semi-circular, rectangular, rhomboid, and the like, and the channels may be formed in a wide range of aspect ratios. It is also noted that a device having a plurality of microchannels laser-ablated thereon falls within the spirit of the present invention.

Figure 13:
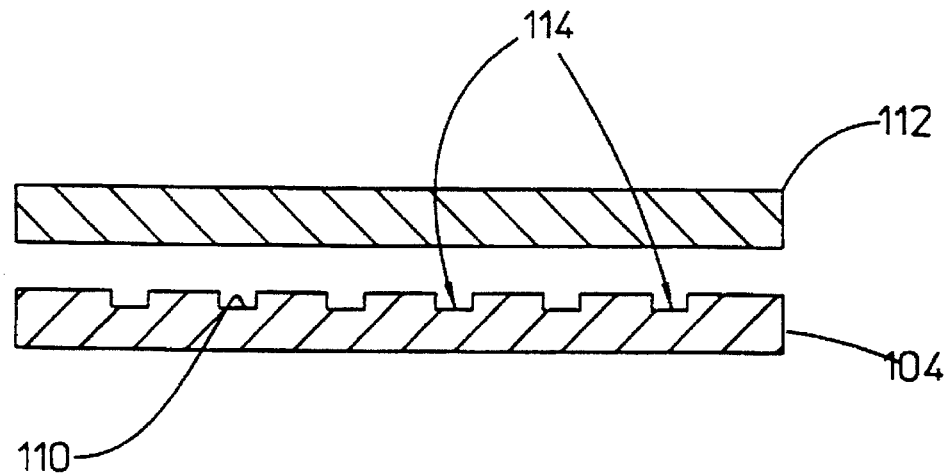
FIG. 13 is a cross-sectional side view of the miniaturized column device of FIG. 10, taken along lines IV—IV and showing formation of a separation compartment according to the invention.

Referring particularly to FIGS. 10 and 13, a cover member (e.g., a plate) 112 is arranged over said first planar surface 106 and, in combination with the laser-ablated microchannel 110, forms an elongate separation compartment 114. Cover plate 112 may be formed from any suitable substrate, such as polyimide.

Under the invention, cover plate 112 may be fixably aligned over the first planar surface 106 to form a liquid-tight separation compartment by using pressure sealing techniques, by using external means to urge the pieces together (such as clips, tension springs or associated clamping apparatus) or by using adhesives well known in the art of bonding polymers, ceramics and the like. The cover plate is firmly secured to the substrate to form a liquid-tight seal so that any fluid in the microchannel will not contact any of the antennas.

Referring to FIGS. 10–12, a particular embodiment of the invention is shown wherein cover plate 112 further comprises apertures ablated therein. In this regard, a first aperture communicates with the separation compartment 114 at a first end 116 thereof to form an inlet port 118 enabling the passage of fluid from an external source into said separation compartment. A second aperture communicates with the separation compartment 114 at a second end 120 thereof to form an outlet port 122 enabling passage of fluid from the separation compartment to an external receptacle. Accordingly, a miniaturized column device is formed having a flow path extending from the first end 116 of the separation compartment and passing to the second end 20 thereof, whereby liquid phase analysis of samples may be carried out using techniques well known in the art.

Referring still to FIGS. 10–12, a particular embodiment of the invention is shown comprising sample introduction means laser-ablated into both the substrate 104 and cover plate 112. Such means may include an internally ablated by-pass channel 124 in the substrate 104 and additional apertures 126 and 128 in cover plate 112 arranged to cooperate with first and second ends (indicated at 130 and 132 respectively) of the by-pass channel 124. This sample introduction means will enable a wide variety of sample introduction techniques to be practiced under the invention. It is also contemplated that external valving and injection means communicate with the separation device by butt-coupling to the laser-ablated apertures. However, any other suitable methods of connection known in the art may easily be adapted to the invention.

The use of substrates such as polyimides in the construction of miniaturized columns under the invention allows the possibility of using refractive-index (RI) detection to detect separated analytes of interest passing through the subject columns. In this regard, the provision of an associated laser diode which emits radiation at a wavelength where polyimide is "transparent" (such as at >450 nm) allows for a detection setup where no additional features need to be ablated in the column devices.

Referring to FIGS. 10–12, in a preferred embodiment of the invention, detection means may be ablated into the substrate 104 and cover plate 112, where said detection means is disposed substantially downstream of the first end 116 of the separation compartment 114. An aperture 134 may be ablated through substrate 104 and aperture 36 may be likewise formed in cover plate 112. In this manner, electrodes (not shown) may be connected to the miniaturized column device via the apertures 134 and 136 to detect separated analytes of interest passing through the separation compartment by electrochemical detection techniques. In a similar manner, electrical connections can be provided for the antennas and electrical connectors (e.g., 16A, 18A, etc. in FIG. 1).

The ability to exert rigid computerized control over the present laser ablation processes enables extremely precise microstructure formation, which, in turn, enables the formation of miniaturized columns having features ablated in two substantially planar components wherein those components may be aligned to define a composite separation compartment of enhanced symmetry and axial alignment. In this regard, it is contemplated to provide a further embodiment of the invention wherein laser ablation is used to create two component halves which, when folded or aligned with one another, define a single miniaturized column device. In such embodiments, the antennas can be located on only one half or on both halves.

Figure 14:
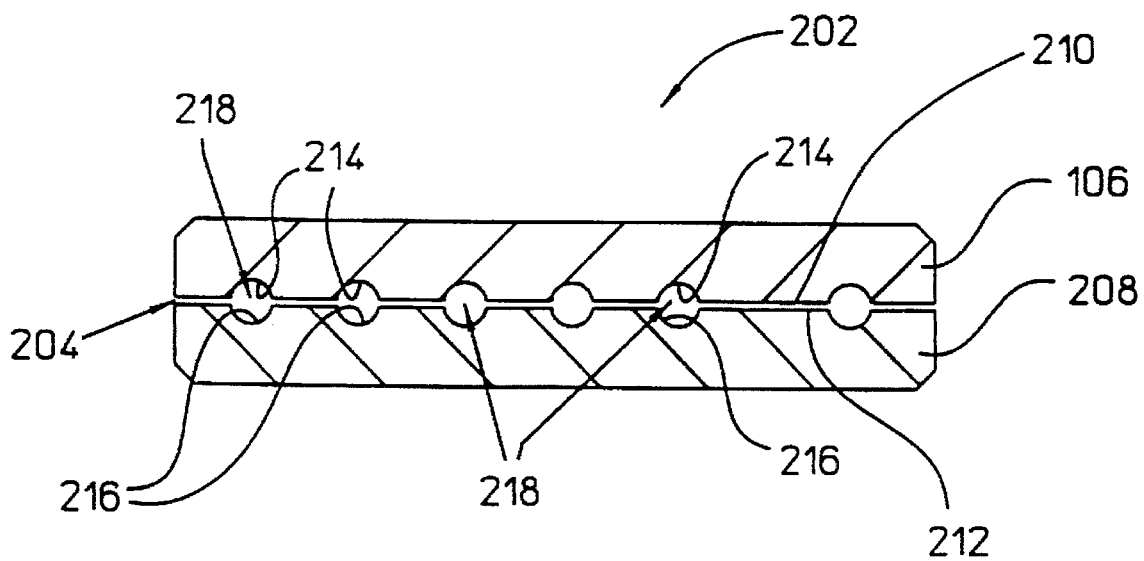
FIG. 14 is a cross-sectional axial view of another embodiment of a miniaturized column device of the present invention (with the electrical components being omitted for clarity purposes), wherein the device has two similar halves.

Referring now to FIG. 14, a miniaturized column for liquid phase analysis of a sample is generally indicated at 202. Again, for clarity of description, the electrical connectors, antennas, and other electrical components are not shown. The miniaturized column 202 is formed by providing a support body 204 having first and second component halves indicated at 206 and 208 respectively. The support body may comprise a substantially planar substrate such as a polyimide film which is both laser ablatable and flexible so as to enable folding after ablation; however, the particular substrate selected is not considered to be limiting in the invention.

The first and second component halves 206 and 208 each have substantially planar interior surfaces, indicated at 210 and 212 respectively, wherein miniaturized column features may be laser ablated. More particularly, a first microchannel pattern 214 is laser ablated in the first planar interior surface 210 and a second microchannel pattern 216 is laser ablated in the second planar interior surface 212. In this invention, said first and second microchannel patterns are ablated in the support body 204 so as to provide the mirror image of each other.

A separation compartment 218, comprising an elongate bore defined by the first and second microchannel patterns 214 and 216 may be formed by aligning (such as by folding) the first and second component halves 206 and 208 in facing abutment with each other. In the practice of the invention, the first and second component halves may be held in fixable alignment with one another to form a liquid-tight separation compartment using pressure sealing techniques, such as by application of tensioned force, or by use of adhesives well known in the art of liquid phase separation devices. It is further contemplated under the invention to form first and second microchannels 214 and 216 having semi-circular cross-sections whereby alignment of the component halves defines a separation compartment 218 having a highly symmetrical circular cross-section to enable enhanced fluid flow therethrough; however, as discussed above, a wide variety of microchannel geometries are also within the spirit of the invention.

A wide variety of associated detection means may then be interfaced to the separation compartment 218 to detect separated analytes of interest passing therethrough. For example apertures can be laser ablated on the substrate to provide connection of electrodes to the miniaturized column. Electrical connection to the electrical components (such as antennas and electrical connectors (e.g., 18B', 20C' in FIG. 1) can be provided in a similar manner.

It is understood that all of the antennas can be positioned on one half or on both halves of the body. Further, it is also contemplated that the antennas are so positioned that the two poles of a set of antennas are located on the same half or each on a different half. In this way, electric fields can be created between antennas on the same half or on different halves (e.g., the electric field between two antennas positioned at a generally diagonal relationship in a separation compartment with a square cross section).

Figure 15:
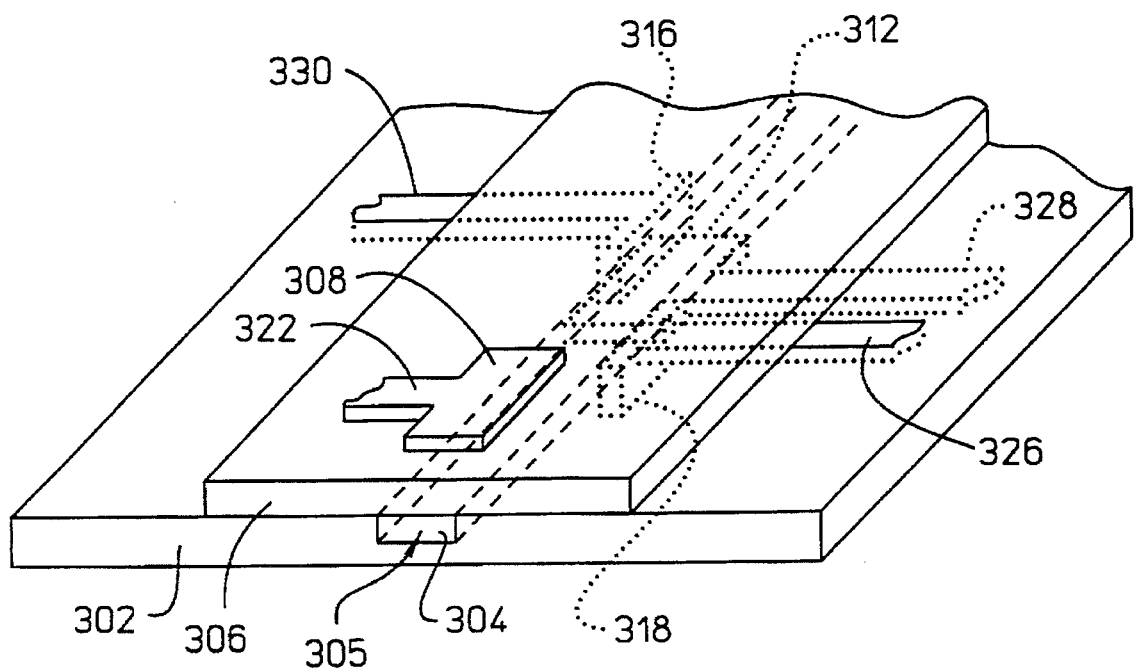
FIG. 15 is an isometric representation of a portion of another embodiment of the present invention, showing hidden features.
Figure 16:
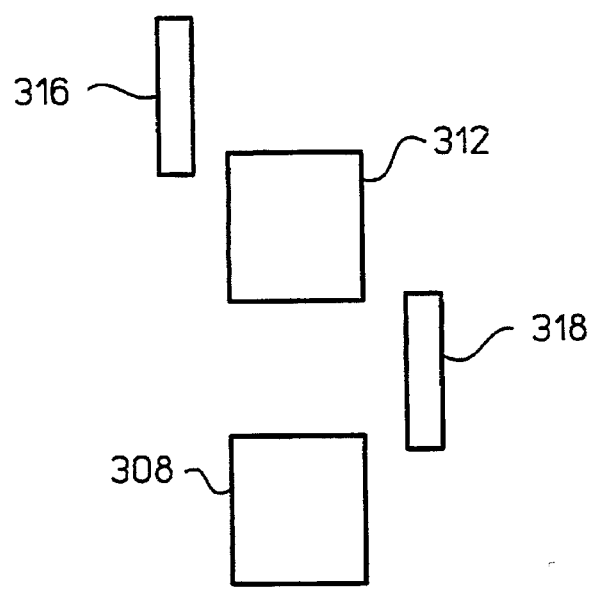
FIG. 16 is a schematic top view of the antennas of the embodiment shown in FIG. 15.
Figure 17:
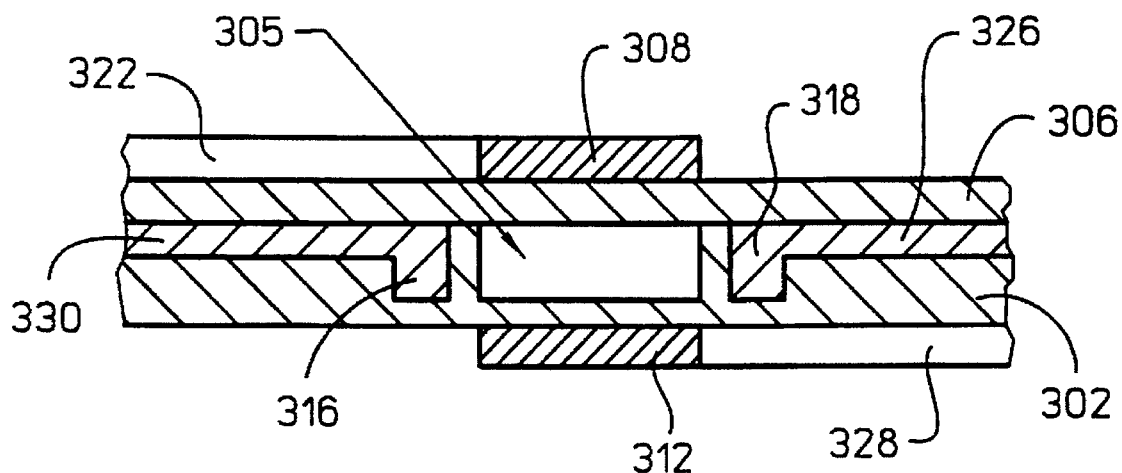
FIG. 17 is a schematic representation of the end view of the embodiment of FIG. 15, showing hidden features.

FIGS. 15–17 illustrate an example of a MCD with antennas on all four sides of a separation compartment. In this embodiment, a substrate 302 has a microchannel 304 micromachined thereon. Microchannel 304 and a cover member 306 defines a separation compartment 305 with a rectangular cross section. Considering the cover member 306 to be on "top" of the substrate 302, an antenna 308 is located on top of the cover member over the microchannel 304 while an antenna 312 is on the bottom of the substrate under the microchannel. Additionally, antennas 316 and 318 have been formed in the substrate 302, each being proximate and on an opposing side of the microchannel 304. The antennas 308, 318, 312, 316 are arranged in that order along the elongate dimension of the separation compartment 305. Electrically conductive bridges 322, 326, 328, 330 connect the antennas 308, 318, 312, 316 respectively to oscillating voltage sources (not shown) through electrical connectors (not shown). Additional antennas (not shown in the figures) are also located in the MCD to form a regular repetitive pattern of arrangement of antennas at the four sides and along the separation compartment. FIG. 16 shown the schematic top view of the arrangement of the antennas. FIG. 17 presents a schematic end view showing the relative positions of the antennas. In FIG. 17, the hidden antennas 318, 312, 316 are also shown. In this embodiment, the voltages of the antennas can be made to oscillate so that one antenna leads in phase the next (downstream) antenna.

Figure 18:
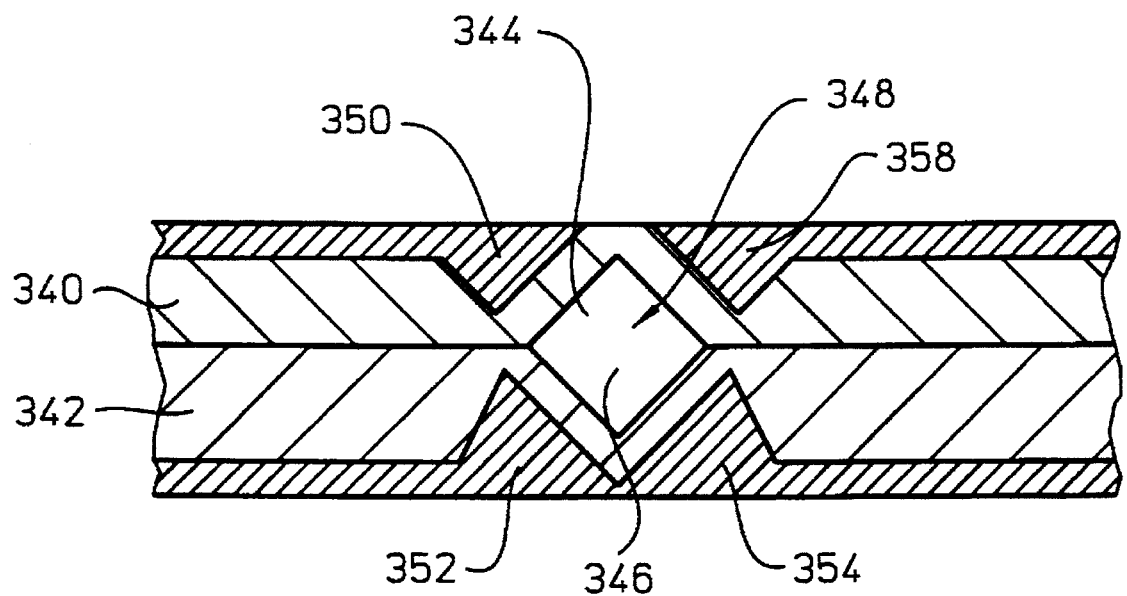
FIG. 18 is a schematic representation of the end view of another embodiment of the present invention.

The antennas can have a variety of shapes. As an example, FIG. 18 shows an embodiment wherein the antennas have a triangular cross section. In FIG. 18, the MCD has two halves formed from substrates 340, 342, which have microchannels 344, 346 defining a separation compartment 348 (which has a rhombic cross section). Antennas 350, 358 are located in substrate 340 and antennas 352, 354 are located in substrate 342 on the four sides of the separation compartment 348. The antennas 350, 352, 354, 358 are arranged along the separation compartment 348 in order similar to antennas 308, 318, 312, 316 in FIG. 15. The microchannels and the grooves, depressions, and the like for electrical components (such as antennas, bridges, and electrical connectors) can be formed, for example, by laser ablation. Then metal can be deposited in these grooves, depressions, and the like to form the electrical components.

Another preferred embodiment is a planar column wherein the separation compartment (defined by a microchannel) has a straight elongate dimension instead of an arcuate one. Such a planar column would have an appearance similar to those of, for example, FIGS. 1, 13, 14, 15, 17, and 18 except that the separation compartment will have no turns. This embodiment is practicable because the present highly efficient separation technique enables short columns (e.g., 1 to 5 cm long) to be used.

The following example provides an illustration of how the miniaturized 434 analytical apparatus of the present invention is used, the following example is provided.

Example

Three proteins are separated by a planar miniaturized column analytical apparatus similar to that of FIG. 1. The three proteins are trypsin inhibitor (TI), ovalbumin (OA), and α-chymotrypsinogen (CTN). TI has an isoelectric point (pI) of 4.6 and a mass of 20.1 kD. OA also has a pI of 4.6 but a mass of 45 kD. CTN has a pI of 9.5 and a mass of 25 kD. From the Brookhaven data base, the size/shape factor of CTN and TI are essentially identical, and therefore could not be separated by a size-based electrophoretic separation. OA and TI are iso-pI and therefore could not be separated by a charge-based electrophoretic separation. All three of these proteins can be separated by capillary zone electrophoresis under the following conditions:

$L_{eff}$=25 cm
$L_{total}$=33.5 cm
Field=–500 V/cm
Buffer=10 mM citrate, pH 3.0
Electro-osmotic flow (EOF)=–1.4 mm/sec
Capillary: 25 micron/125 micron bubble capillary, with bovine serum albumin covalently coated.

Under these conditions, the proteins were completely baseline separated. Their mobilities under these buffer conditions were determined to be: TI=$2.1 \times 10^{-4}$ cm2/Volt.sec, OA=$2.2 \times 10^{-4}$ cm2/Volt.sec, and CTN=$2.5 \times 10^{-4}$ cm2/Volt.sec, where the solute mobility is calculated from:

$$\mu_{total} = \mu_{eof} + \mu_{epm} \text{ then } \mu_{epm} = \mu_{total} - \mu_{eof}$$

where:

$\mu_{total}$=total observed mobility
$\mu_{eof}$=electroosmotic mobility
$\mu_{epm}$=electrophoretic mobility given that mobility is defined as $$\mu = \frac{\text{Velocity(cm/sec)}}{\text{Field(Volts/cm)}}$$

For separating these species using the present invention, a channel of dimensions 20 microns with total length of 1 cm, and having antennas spaced at 5 microns is preferred. At one instant, on one side of the channel, one antenna sits at 20 Volts, while at the other side, one antenna sits at −20 Volts. The effective field within the channel, at 25% effect of the field drop between the antennas, is then 5 kVolts. The absolute distance travels by the solute between the activation of two neighboring antennas is about 7 microns. From the following relationship which defines the clock rate of the AC signal:

$$\Delta t = \frac{\text{moving distance}}{\text{moving speed}} = \frac{\text{moving distance}}{\text{mobility} * \text{field strength}}$$

where:
Δt=clock time (sec)
moving distance=the total distance the solute travels (in cm)

$$\text{mobility} = \mu \text{ (defined above)} \in \frac{cm^2}{Volts*sec}$$

$$\text{field strength} = \frac{Volts}{cm}$$

then the clock rate Θ, is the reciprocal of clock time; 1/Δt (in kHz). Given the defined moving distance at 7 microns, and the field at 5 kVoplts, by inserting the solute mobilities determined under the defined conditions of 10 mM citrate, pH 3.0, the separation would occur as follows: the alternating 20 Volts AC signal would be set first 2.0 kHz (500 μs clock rate) for a duration of 20 seconds, thus allowing the α-chymostrysinogen to be specifically separated from ovalbumin and trypsin inhibitor. Next, the alternating 20 Volts AC signal would be set at 1.5 kHz (667 μs clock rate) for 20 seconds, so that ovalbumin is specifically moved down the separation channel to the point of detection. Finally, the alternating 20 Volts AC signal would be set at 1.0 kHz (1 msec clock rate) for 20 seconds, allowing the trypsin inhibitor to move down the channel past the point of detection. Under the described conditions, the linear velocities of the three proteins are calculated to be 13 mm/sec, 11 mm/sec and 0.7 mm/sec respectively.

While the present invention has been described with reference to specific preferred embodiments, it is understood that the description and examples included herein are intended to illustrate and not limit the scope of the invention. Modifications will be apparent to one skilled in the art. For example, although electrophoretic applications are described, other columnar application such as chromatography wherein electrically charged analytes are being analyzed.

What is claimed is:

1. A miniaturized column analytical apparatus comprising:
   (a) a miniaturized column device comprising:
      (i) a body having an elongate separation compartment having first and second opposing sides along the elongate dimension;
      (ii) two or more sets of spaced apart antennas positioned along the opposing sides of the separation compartment, each set containing a plurality of antennas, one antenna from each set being associated with at least one antenna from each of the other sets to form repeating sequences of antennas along the separation compartment on said sides of the separation compartment, each set of the antennas being associated with a different oscillating alternating current electrical potential to provide a plurality of oscillating electric fields along the elongate separation compartment to draw a target substance along said elongate separation compartment toward an exit end thereof, and
   (b) a detector for detecting the target substance passing through the elongate separation compartment.

2. The apparatus of claim 1 wherein the antennas are spaced from the separation compartment so that the antennas do not contact any medium in the separation compartment.

3. The apparatus of claim 1 wherein the oscillating electrical potentials have a sinusoidal wave form.

4. The apparatus of claim 1 wherein the oscillating electrical potentials have a square wave form.

5. The apparatus of claim 1 wherein the apparatus has 2 to 6 sets of antennas.

6. The apparatus of claim 1 further comprising a power supply for providing oscillating electrical potentials to the antennas such that each set of antennas is associated with a different oscillating electrical potential.

7. The apparatus of claim 6 wherein the power supply is adapted to be capable of supplying different sets of antennas with oscillating electrical potentials different in phase.

8. The apparatus of claim 7 wherein the power supply is adapted to be capable of supplying different sets of antennas with oscillating electrical potentials such that electrical potential of an antenna differs in phase from its neighboring antennas on the same side of the separation compartment by 360°/n, where n is the number of sets of antennas so that the antennas on the same side form a repeating sequence with substantially equal phase shift between neighboring antennas.

9. The apparatus of claim 8 wherein the separation compartment has a downstream direction and the power supply is adapted to be capable of supplying electrical potential such that the electrical potential of an antenna leads that of the antenna closest and downstream thereto on the opposing side by a phase difference of 180°/n, where n is the number of sets of antennas so that the antennas on the two opposing sides form a repeating sequence of phase difference.

10. The apparatus of claim 1 wherein the power supply is adapted to be capable of supplying electrical potential such that the oscillating electrical potentials each has a peak to peak voltage of up to 100V.

11. The apparatus of claim 10 wherein the power supply is adapted to be capable of supplying electrical potential such that the oscillating electrical potentials each has a peak to peak voltage of up to 1V.

12. The apparatus of claim 1 wherein the body includes a substrate having first and second substantially planar surfaces facing away from each other and a cover member arranged over the first planar surface, the separation compartment being defined by the cover member and a microchannel in the first planar surface of the substrate.

13. The apparatus of claim 12 wherein the substrate is selected from the group consisting of polymeric material, ceramic materials, and combinations thereof.

14. The apparatus of claim 12 wherein the cover member has two substantially planar surfaces facing away from each other and having microchannel laser-ablated on the surface facing the substrate so that the microchannel on the cover member and the microchannel on the substrate match to define the separation compartment.

15. The apparatus of claim 12 wherein the cover member and the substrate each has antennas secured thereon, said antennas having oscillating electrical potentials to provide migrating electric fields along the separation compartment.

16. The apparatus of claim 12 wherein all the antennas are secured to the substrate along two opposing sides of the microchannel on the substrate.

17. The apparatus of claim 12 wherein the microchannel is made on the substrate by laser ablation.

18. The apparatus of claim 1 wherein the separation compartment has four sides and the antennas are secured to the substrate along all four sides of the separation compartment.

19. A miniaturized column device for moving a target substance through an elongate compartment comprising:
   (i) a substrate having first and second substantially planar surfaces facing away from each other, said substrate having a microchannel in the first planar surface;
   (ii) a cover member arranged over the first planar surface, said cover member in combination with the microchannel defining the elongate compartment, said elongate compartment having first and second opposing sides along its elongate dimension; and
   (iii) two or more sets of spaced apart antennas positioned along the opposing sides of the compartment, each set containing a plurality of antennas, one antenna from each set being associated with at least one antenna from each of the other sets to form repeating sequences of antennas along the elongate compartment at said opposing sides such that any two neighboring antennas from the same side and the antenna from the opposing side closest to said two neighboring antennas are in a triangular configuration, each set of the antennas being associated with a different oscillating electrical potential to provide a plurality of oscillating electric fields along the elongate compartment to draw the target substance along said elongate compartment.

20. A method for analyzing a target substance, comprising:
   (a) placing the target substance in a miniaturized elongate compartment;
   (b) providing a different oscillating alternating current electrical potential on each of two or more sets of antennas along the elongate compartment to result in a plurality of oscillating electric fields to draw the target substance along the elongate compartment; and
   (c) detecting the target substance proximate an exit end of the elongate compartment.

21. The method of claim 20 wherein more than one target substance is suspected to be present in a sample to be analyzed and step (b) of the method comprises tuning to a different frequency of oscillating potential for each different target substance to separate the different target substances as they pass through the elongate compartment.

22. The method of claim 20 wherein the oscillating electrical potentials have a sinusoidal wave form.

23. The method of claim 20 wherein in step (b) the oscillating potentials are tuned from a high frequency to a low frequency to obtain an optimal frequency for drawing the target substance through the elongate compartment.

24. A method for making a miniaturized column device, comprising:
   (a) micromachining a substrate having first and second substantially planar surfaces facing away from each other to result in a microchannel in the first planar surface;
   (b) arranging over the first planar surface a cover member which in combination with the microchannel defining an elongate separation compartment having first and second opposing sides along an elongate separation dimension and positioning two or more sets of spaced apart antennas along the opposing sides of the separation compartment, each set containing a plurality of antennas, one antenna from each set being associated with at least one antenna from each of the other sets to form repeating sequences of antennas along the separation compartment at said opposing sides; and
   (c) connecting a power supply means to the antennas such that each set of the antennas is associated with a different oscillating alternating current electrical potential to result in a plurality of oscillating electric fields along the elongate separation compartment capable of drawing a target substance along said elongate separation compartment so that the target substance can be detected proximate an exit end of the elongated separation compartment.

25. The method of claim 24 wherein laser ablation is used in micromachining the substrate to form the microchannel.

26. A miniaturized column analytical apparatus comprising:
   (a) a miniaturized column device comprising:
      (i) a body having an elongate separation compartment having first and second opposing sides along the elongate dimension;
      (ii) two or more sets of spaced apart antennas positioned along the opposing sides of the separation compartment, each set containing a plurality of antennas, one antenna from each set being associated with at least one antenna from each of the other sets to form repeating sequences of antennas along the separation compartment on said sides of the separation compartment, each set of the antennas being associated with a different oscillating electrical potential to provide a plurality of oscillating electric fields along the elongate separation compartment to draw a target substance along said elongate separation compartment toward an exit end thereof, wherein each set of antennas has two subsets each having electrical potential that is a mirror image of the other in amplitude; and
   (b) a detector for detecting the target substance passing through the elongate separation compartment.

27. The apparatus of claim 26 wherein the antennas are arranged such that the antennas of the the two subsets of antennas are positioned on opposite sides of the separation compartment and such that each antenna opposes and being immediately proximate to antennas not of the same set.

28. The apparatus of claim 26 wherein the antennas are arranged such that the antennas of both subsets from any one set of antennas are positioned on the same side of the separation compartment and such that each antenna opposes and being immediately proximate to antennas not of the same set.

29. The apparatus of claim 26 wherein the antennas are spaced apart in regular intervals on each of the opposing sides of the separation compartment such that any two neighboring antennas from the same side and the antenna from the opposing side closest to said two neighboring antennas are in a triangular configuration.

30. A method for analyzing a target substance, comprising:
   (a) placing the target substance in a miniaturized elongate compartment having opposing sides and a downstream direction;

(b) providing a different oscillating electrical potential on each of two or more sets of antennas along the elongate compartment to result in a plurality of oscillating electric fields to draw the target substance along the elongate compartment, such that the electrical potential of an antenna leads the electrical potential of the antenna closest and downstream thereto on the opposing side by a phase difference of 180°/n, where n is the number of sets of antennas so that the antennas on the two opposing sides form a repeating sequence of phase difference; and (c) detecting the target substance proximate an exit end of the elongate compartment; wherein the elongate compartment, the antennas being positioned along the opposing sides.

* * * * *